US012740723B2

(12) United States Patent
Peumans et al.

(10) Patent No.: US 12,740,723 B2
(45) Date of Patent: Sep. 22, 2026

(54) COLLECTING DEVICE FOR COLLECTION OF PARTICLES, A SAMPLE COLLECTOR, AND AN ANALYSIS INSTRUMENT

(71) Applicant: IMEC VZW, Leuven (BE)

(72) Inventors: Peter Peumans, Herfelingen (BE); Benjamin Jones, Kessel-Lo (BE); Xavier Rottenberg, Kessel-Lo (BE); Chengxun Liu, Heverlee (BE); Ahmed Taher, Heverlee (BE)

(73) Assignee: IMEC VZW, Leuven (BE)

( * ) Notice: Subject to any disclaimer, the term of this patent is extended or adjusted under 35 U.S.C. 154(b) by 670 days.

(21) Appl. No.: 18/031,662

(22) PCT Filed: Oct. 14, 2021

(86) PCT No.: PCT/EP2021/078509

§ 371 (c)(1),
(2) Date: Apr. 13, 2023

(87) PCT Pub. No.: WO2022/079195

PCT Pub. Date: Apr. 21, 2022

(65) Prior Publication Data

US 2023/0380720 A1 Nov. 30, 2023

(30) Foreign Application Priority Data

Oct. 14, 2020 (EP) .................................... 20201787
Apr. 26, 2021 (EP) .................................... 21170431

(51) Int. Cl.
*A61B 5/08* (2006.01)
*A61B 5/00* (2006.01)
(Continued)

(52) U.S. Cl.
CPC ............ *A61B 5/082* (2013.01); *A61B 5/0082* (2013.01); *A61B 5/091* (2013.01); *A61B 5/097* (2013.01);
(Continued)

(58) Field of Classification Search
CPC ....... A61B 5/082; A61B 5/0082; A61B 5/097; A61B 5/09; G01N 1/2208; G01N 33/497;
(Continued)

(56) References Cited

U.S. PATENT DOCUMENTS 5,304,125 A 4/1994 Leith
6,101,886 A 8/2000 Brenizer et al.
(Continued)

FOREIGN PATENT DOCUMENTS

WO WO-2017/001374 A1 1/2017
WO WO-2018/126119 A1 7/2018
(Continued)

OTHER PUBLICATIONS

Maldonado-Garcia, et al: "Chip-Scale Aerosol Impactor with Integrated Resonant Mass Balances for Real Time Monitoring of Airborne Particulate Concentrations", $28^{th}$ IEEE International Conference on Micro Electro Mechanical Systems (MEMS), pp. 885-888, 2015.
(Continued)

*Primary Examiner* — Eric F Winakur
*Assistant Examiner* — Sienna C Pyle
(74) *Attorney, Agent, or Firm* — MOSER TABOADA

(57) ABSTRACT

A collecting device (200) for collection of particles and presentation of collected particles for analysis comprises: a first layer (202) and a second layer (220) spaced apart for defining a particle collection chamber (240); wherein the first layer (202) is configured to receive a flow of air (104) carrying airborne particles, wherein the first layer (202)
(Continued)

comprises a plurality of inlet nozzles (210) configured to extend through the first layer (202) for transporting the flow of air (104) therethrough; wherein the inlet nozzles (210) are configured to face a first surface (222) of the second layer (220) for capturing airborne particles in the flow of air (104) entering the particle collection chamber (240) by impaction of airborne particles; wherein the collecting device (200) is configured to provide optical access for performing a measurement, based on light, of airborne particles collected in the particle collection chamber (240).

19 Claims, 11 Drawing Sheets

(51) Int. Cl.
*A61B 5/091* (2006.01)
*A61B 5/097* (2006.01)
*G01N 1/22* (2006.01)
*G01N 33/497* (2006.01)

(52) U.S. Cl.
CPC ......... *G01N 1/2208* (2013.01); *G01N 33/497* (2013.01); *G01N 33/4975* (2024.05); *G01N 2001/2244* (2013.01); *G01N 2800/12* (2013.01)

(58) Field of Classification Search
CPC ....... G01N 33/4975; G01N 2001/2244; G01N 2800/12
See application file for complete search history.

(56) References Cited

U.S. PATENT DOCUMENTS 7,135,060 B2 11/2006 Jordan, Sr. et al.
7,631,567 B1 * 12/2009 Hill ...................... G01N 1/2202 73/863.22
2004/0118222 A1 6/2004 Cornish et al.
2005/0279181 A1 12/2005 Trakumas et al.
2007/0173731 A1 7/2007 Meka et al.
2008/0061238 A1 3/2008 Hok et al.
2009/0275113 A1 * 11/2009 Maltezos ............ B01L 3/50851 435/283.1
2010/0062415 A1 * 3/2010 Schwoebel ............ G01N 21/07 435/5
2010/0268106 A1 10/2010 Johnson et al.
2012/0255375 A1 10/2012 Kwok et al.
2012/0302907 A1 11/2012 Palmskog et al.
2013/0078733 A1 * 3/2013 Holmes ............... B01L 3/50825 422/524
2013/0192463 A1 8/2013 Wu et al.
2013/0319239 A1 12/2013 Takenaka et al.
2015/0010902 A1 1/2015 Takenaka et al.
2016/0223435 A1 8/2016 Takenaka et al.
2016/0249828 A1 9/2016 Blanton et al.
2017/0059466 A1 3/2017 Park
2017/0215764 A1 8/2017 Hamilton
2017/0299477 A1 10/2017 Milton et al.
2018/0164283 A1 6/2018 Godula-Jopek et al.
2020/0158603 A1 5/2020 Scialo et al.
2020/0221973 A1 7/2020 Höjer
2020/0245899 A1 8/2020 Heanue et al.
2020/0278275 A1 9/2020 Turgul et al.
2021/0101437 A1 4/2021 Birks et al.
2023/0380720 A1 11/2023 Peumans et al.

FOREIGN PATENT DOCUMENTS

WO WO-2018/172760 A1 9/2018
WO WO 2022/079195 A1 4/2022

OTHER PUBLICATIONS

Pardon, et al: “Aerosol sampling using an electrostatic precipitator integrated with a microfluidic interface”, Sensors and Actuators B: Chemical, vol. 212, pp. 344-352, 2015.
Marple, et al: “Impactor Design”, Atmospheric Environment, vol. 10, No. 10, 1976. pp. 891-896.
International Search Report & Written Opinion for Application No. PCT/EP2021/078509 dated Jan. 26, 2022.

* cited by examiner

COLLECTING DEVICE FOR COLLECTION OF PARTICLES, A SAMPLE COLLECTOR, AND AN ANALYSIS INSTRUMENT

CROSS-REFERENCE TO RELATED APPLICATIONS

This application claims the benefit of European Patent Application No. EP20201787.7 filed 14 Oct. 2020 and European Patent Application No. EP21170431.7 filed 26 Apr. 2021, the contents of which are hereby incorporated by reference herein.

TECHNICAL FIELD

The present inventive concept relates to a collecting device for collection of particles. In particular, the present inventive concept relates to collection of particles for facilitating analysis of the particles using a measurement based on light, such as a fluorescence measurement.

BACKGROUND

Fast analysis of particles, such as detecting presence of particular substances, is of high interest in various applications. For instance, screening for infectious diseases, such as influenza and severe acute respiratory syndrome coronavirus 2 (SARS-CoV-2), in a fast and inexpensive manner may allow screening to be performed frequently and enable quick identification of persons carrying disease. Such identification of diseased persons would allow measures to be taken for preventing or reducing spreading of the disease.

Diseases like influenza and SARS-CoV-2 are believed to be primarily spread through droplets and aerosols produced during normal breathing, talking, coughing and sneezing. Thus, it would be of interest to provide efficient capture of particles in air exhaled by persons and robust analysis of presence of substances of interest within the exhaled air so as to identify whether a person carries a disease or not.

SUMMARY

An objective of the present inventive concept is to provide simple and efficient capture of particles and facilitate analysis of the collected particles.

This and other objectives of the present inventive concept are at least partly met by the invention as defined in the independent claims. Preferred embodiments are set out in the dependent claims.

According to a first aspect, there is provided a collecting device for collection of particles and presentation of collected particles for analysis, said collecting device comprising: a first layer and a second layer, wherein the first layer and the second layer are arranged to be spaced apart for defining a particle collection chamber between the first and the second layer; wherein the first layer comprises a first surface configured to receive a flow of air carrying airborne particles and a second surface facing the second layer, wherein the first layer comprises a plurality of inlet nozzles having a first end at the first surface of the first layer and a second end at the second surface of the first layer, wherein the inlet nozzles are configured to extend through the first layer for transporting the flow of air therethrough from the first end to the second end; wherein the second ends of the inlet nozzles are configured to face a first surface of the second layer for capturing airborne particles in the flow of air entering the particle collection chamber through the second ends of the inlet nozzles by impaction of airborne particles on the first surface of the second layer; wherein the collecting device is configured to provide optical access for performing a measurement, based on light, of airborne particles collected in the particle collection chamber at a first measurement position arranged such that the second layer is between the second side of the particle collection chamber and the first measurement position or at a second measurement position, which is arranged at an opposite side to the first measurement position in relation to the second side of the particle collection chamber.

Thanks to the collecting device, an efficient capturing of airborne particles may be provided in a particle collection chamber. The plurality of inlet nozzles may be designed so as to provide a high impaction capturing efficiency. Further, thanks to the collecting device comprising a plurality of inlet nozzles, the collecting device facilitates breathing through the inlet nozzles of the collecting device without requiring a high supply pressure to be provided by the person breathing through the collecting device.

The collecting device thus enables capturing of particles in a particle collection chamber in an efficient manner so as to ensure that particles captured on the particle collection chamber may be analyzed e.g. for determining presence of a substance. The collecting device provides a sample collection of particles from a human being so as to highly reduce discomfort in the sample collection compared e.g. to a sample being collected by a nasal or throat swab.

As used herein, capturing of airborne particles by "impaction" should be construed as particles being removed from the flow of air by forcing the flow of air to change direction. Thanks to the flow of air being forced to change direction, momentum of particles having a certain size will cause the particles not to follow the flow of air in its change of direction and instead the particles will be captured on a collection surface. The capturing of airborne particles may involve capturing of aerosols but may also or alternatively involve capturing of larger droplets in the flow of air.

The flow of air may be received by the collecting device by the human being blowing directly into an apparatus holding the collecting device, such as through a mouthpiece of the apparatus. Hence, the flow of air may be provided directly from exhalation by the human being. However, it should be realized that the flow of air may alternatively be received indirectly from the human being, e.g. by the human being exhaling into a bag and by the flow of air being provided by the bag towards the collecting device. Further, the flow of air need not necessarily originate from a human being. Rather, the flow of air may be based on exhale from another living being or may be based on air being collected in any environment and being provided into an apparatus holding the collecting device. A required pressure for passing the flow of air through the collecting device need thus not be provided by the exhale of a human being but may be provided by any component causing a flow of air.

In the following, the flow of air may be referred to as originating from exhale of a human being, but it should be realized that the flow of air may alternatively be provided in other manners.

The second ends of the inlet nozzles being configured to face the first surface of the second layer implies that the flow of air passing through the inlet nozzles will be directed towards the first surface of the second layer so as to allow impaction thereon. This does not necessarily mean that a continuous first surface of the second layer is present in relation to an entire cross-section of the second end of the inlet nozzle. Rather, the second layer may comprise outlet nozzles, wherein the outlet nozzles have a first end at the first surface of the second layer and a second end at a second surface of the second layer and the outlet nozzles are configured to extend through the second layer for transporting the flow of air therethrough from the first end to the second end. The inlet nozzles and the outlet nozzles may be arranged such that the outlet nozzles are not collinear with the inlet nozzles. However, it should be realized that there may be an overlap between edges of the inlet nozzles and outlet nozzles, such that a projection of the second end of the inlet nozzle facing the first surface of the second layer would overlap with an end of the outlet nozzles in the first surface of the second layer. It may be preferred that there is no overlap between edges of the inlet nozzles and outlet nozzles, since this would be associated with a relatively large change of direction of the flow of air, which may be advantageous in providing an efficient capturing of particles.

The collected particles may be directly analyzed while being arranged on the first surface of the second layer. Thus, the sample may be directly analyzed and there may be no need to move the collected particles for analysis. The collected particles may however undergo one or more steps of reactions while being arranged on the first surface of the second layer before a measurement based on light for analyzing the collected particles is made.

According to an embodiment, the airborne particles may be borne e.g. by aerosols and/or by droplets in the air exhaled by a person. The airborne particles may further comprise substance(s) of interest, such that analysis of the collected particles may include the particles being subject to reactions for exposing the substance(s) of interest to enable detection of substance(s) of interest in a measurement.

Thanks to reactions and measurements being performed while the collected particles are arranged on the first surface of the second layer on which the collected particles are captured, the collecting device facilitates a fast analysis of a sample being made.

For instance, an analysis result of presence of SARS-CoV-2 may be provided using the collecting device within five minutes of obtaining a sample. This enables for instance screening of people before admitting people to a certain environment, such as screening before admitting entry into an airport, a shop, or a company facility.

Also, thanks to very quickly providing analysis results based on a self-test that the person may perform, testing of people very often is facilitated. In this regard, the use of the collecting device for screening of people may allow people to be screened several times per week, such as every day, such that viral load peaks may be identified. If testing is done only once a week, the viral load peak may be missed such that the testing fails to detect persons having a stage of a disease in which the person is highly infectious. Hence, very frequent testing may be required in order to identify highly infectious people and prevent spreading of a disease.

The particle collection chamber may be adapted for allowing reactions to take place therein and/or for allowing measurements based on light to be performed in relation to the particle collection chamber. Thus, analysis of the collected particles may be performed in the particle collection chamber. As such, the particle collection chamber may also form an analysis chamber and the terms "particle collection chamber" and "analysis chamber" may be used interchangeably herein. However, in some embodiments, the first layer may be removable and replaceable by a cap structure, and in other embodiments, the first layer may be slidable in relation to the second layer. In such embodiments, an analysis chamber may differ from the particle collection chamber in that a wall has been replaced and/or moved. When discussing such embodiments below, distinction between the particle collection chamber and the analysis chamber is made.

It should further be realized that the particle collection chamber and/or the analysis chamber may further be defined by side walls surrounding the particle collection chamber and/or the analysis chamber. The side walls may also provide a spacer for defining a distance between the first layer and the second layer.

The collecting device may be configured in many different manners for providing optical access for performing measurements based on light.

According to an embodiment, the first layer may be removably attached to the second layer, such that the first layer may be removed before the measurements are made. Thus, optical access may be provided by the collected particles being exposed on the first surface of the second layer, such that no obstacles are arranged in an optical path allowing measurements to be performed at the second measurement position. However, it should further be realized that, even though the first layer may be removed, it may be replaced with a cap structure which together with the second layer forms an analysis chamber between the cap structure and the second layer. The cap structure may provide optical access, e.g. by being formed of a transparent material, such as glass, being transparent to wavelengths being used in the measurement based on light. The cap structure may also be adapted for reactions to take place in the analysis chamber, e.g. by the cap structure providing inlet(s) for allowing insertion of reagents into the analysis chamber. Thus, the first layer may be removed and replaced by the cap structure for facilitating reactions that are to take place in the analysis chamber.

Although it is conceivable that the first layer may be removable and possibly be replaceable by a cap structure, it may be beneficial to allow the first layer to be maintained on the collecting device for analysis of collected particles. This implies that no complicated mechanical alterations of the collecting device are needed and facilitates analysis to be performed quickly on the particles collected in the collecting device.

According to an embodiment, the first layer may be slidable in relation to the second layer. This may allow a portion adapted to providing optical access and/or adapted to provide reagent inlet(s) to be slid to be arranged over the first surface of the second layer to define a wall of the analysis chamber. Although the first layer may slidable, the entire first layer may still be adapted to provide optical access, e.g. by the first layer being formed by a transparent or translucent material, being transparent or translucent to wavelengths being used in the measurement based on light.

According to another embodiment, the first layer is fixed to the second layer such that the first and the second layer define an analysis chamber therebetween. Thanks to having a fixed relation between the first layer and the second layer, no mechanical adjustment of the collecting device for defining the analysis chamber is needed, which facilitates fast analysis of particles collected in the collecting device, as reactions to be performed in the analysis chamber and measurements may be initiated directly without requiring any adjustment of the collecting device.

According to another embodiment of providing optical access, the collecting device may be configured to provide optical access by the first and/or second layer being configured to allow light to pass through the layer. Thus, the first and/or the second layer may be formed by a transparent or translucent material, being transparent or translucent to wavelengths being used in the measurement based on light. If a measurement is to be made at the first measurement position, the second layer may be formed by a transparent or translucent material. If a measurement is to be made at the second measurement position, the first layer may be formed by a transparent or translucent material. In this case, the second measurement position may be arranged such that first layer is between the second side of the particle collection chamber and the second measurement position.

It should be realized that the measurement based on light may be configured to determine a quantity of light. In such case, the first and/or the second layer may be formed by a translucent material, which allows light to be passed through the layer. Alternatively, the measurement based on light may be configured to image particles in the analysis chamber or relate detected light to a position in the analysis chamber. In such case, the first and/or the second layer may be formed by a transparent material to allow light to pass mostly unaffected through the first and/or the second layer.

It should further be realized that the first and/or the second layer need not necessarily be transparent or translucent in an entire area related to the analysis chamber. Rather, the first and/or the second layer may comprise portions that are transparent or translucent. For instance, nozzles arranged through the first layer and/or the second layer may allow light to be passed therethrough such that nozzles may be used both for allowing inlets and/or outlets to the analysis chamber and for providing optical access through the first and/or the second layer.

It should be realized that the measurement based on light may be performed in many different ways. The measurement may be performed at either the first measurement position or the second measurement position. Thus, the collecting device may be configured to provide optical access only from one direction in relation to the first surface of the second layer. However, it should be realized that measurements may be performed at both the first measurement position and the second measurement position, such that the collecting device may be configured to provide optical access from both directions in relation to the first surface of the second layer. Also, even though measurements may be performed at only one of the first or the second measurement position, the measurement based on light may include providing illumination light or some other type of stimulation, such as inducing a chemical reaction or providing thermal or electrical energy, for causing output of light. Illumination light may be provided from an opposite side to the measurement position, such that the collecting device may anyway need to be configured to provide optical access from both directions in relation to the first surface of the second layer.

The measurement based on light may comprise detecting light emitted through luminescence. For instance, the measurement based on light may comprise detecting light being emitted based on stimulation by light, such that the measurement based on light may comprise detecting light emitted through fluorescence.

The measurement based on light may comprise illuminating collected particles and/or substance(s) being exposed through reactions in the analysis chamber and detecting light having interacted with the collected particles and/or substance(s). For instance, the measurement based on light may comprise detecting fluorescence to determine presence of a substance. Also, or alternatively, the measurement based on light may comprise detecting absorption of light, transmission of light or detecting scattered light, such as detecting elastically scattered light through e.g. Rayleigh or Mie scattering, or detecting inelastically scattered light through e.g. Raman scattering.

The measurement based on light may additionally or alternatively comprise imaging of particles and/or substance (s) within the analysis chamber. The measurement based on light may thus comprise directly detecting an image based on light interaction in the analysis chamber using an array of photo-sensitive areas. However, the measurement based on light may alternatively comprise detecting interference patterns caused between light being scattered in the analysis chamber and light being unaffected, such that an image may be reconstructed based on detected interference patterns using digital holography imaging.

The first and/or the second layer may include very accurately formed small structures. These structures may be designed for ensuring that a high efficiency of capturing of particles is achieved in the particle collection chamber. Also, the structures may be designed for controlling a supply pressure needed for pushing a flow of air through the collecting device, such that the collecting device may be designed for ensuring that a pressure required to be supplied by the exhalation when a person blows through the collecting device can be easily or relatively easily achieved. Further, the structures may be designed for defining a volume of an analysis chamber, which is small and suitable for providing efficient reactions to be performed on the collected particles within the analysis chamber.

For instance, the inlet nozzles of the first layer may be accurately designed for controlling efficiency of capturing of particles and for controlling a required supply pressure. In this regard, the number of inlet nozzles as well as a size and shape of each inlet nozzle may be controlled through design of the collecting device.

The structures in the first and/or the second layer may e.g. be formed by micromachining, so as to allow forming very accurate small structures in the first and/or the second layer. However, it should be realized that other manufacturing methods may be used, e.g. in dependence of required size of structures in the collecting device. It should further be realized that some parts of the collecting device may not need to include any small structures, and may as such not need to be formed by particular manufacturing methods designed for forming small structures. For instance, the second layer may be formed as a homogeneous substrate or layer and may thus not require particular manufacturing methods to be used.

The collecting device may be formed from a material suitable for micromachining. Thus, the first and/or second layer may be formed from a semiconductor or semiconductor-based material, such as silicon or silicon dioxide.

According to an embodiment, the first and second layers may be configured to extend in parallel. This may be advantageous as it may ensure that a relation between the second ends of the inlet nozzles and the first surface of second layer is identical for all inlet nozzles. However, it should be realized that the first and second layers need not necessarily extend exactly in parallel to each other.

It should further be realized that the first surface of the second layer may be substantially planar for defining a surface for capturing particles by impaction. This may be beneficial in that the second layer may be relatively easy to manufacture. However, according to another embodiment, the first surface of the second layer may be provided with structures protruding from or extending into a planar part of the surface. The second layer may thus define structures which may facilitate capture of particles by impaction and may improve efficiency of capturing of particles. For instance, the second layer may be provided with pillars extending from a planar part of the first surface towards the second ends of the inlet nozzles.

The inlet nozzles may have a circular cross-section. This may facilitate manufacturing of the inlet nozzles and may also enable accurate control of efficiency of capturing of particles by the collecting device. However, it should be realized that the inlet nozzles may have another shape of the cross-section such as rectangular.

The inlet nozzles may have identical shapes and sizes. This may facilitate that efficiency of capturing of particles is similar throughout an area of the particle collection chamber. However, it should be realized that there may be varying shapes between different inlet nozzles, e.g. if it would be desired to have a non-homogeneous distribution of particles being captured in the particle collection chamber.

According to an embodiment, the second layer comprises a plurality of outlet nozzles, wherein the outlet nozzles have a first end at the first surface of the second layer and a second end at a second surface of the second layer and the outlet nozzles are configured to extend through the second layer for transporting the flow of air therethrough from the first end to the second end, wherein a position of the first ends of the outlet nozzles is shifted with respect to a position of the second ends of the inlet nozzles such that the outlet nozzles are not collinear with the inlet nozzles.

Thanks to providing outlet nozzles in the second layer, a direction of the flow of air may not need to be substantially diverted through the collecting device, which may facilitate that the required supply pressure for blowing through the collecting device may be moderate and easily or relatively easily achieved by a person.

The outlet nozzles may be arranged not to be collinear with the inlet nozzles. This may ensure that the flow of air impacts on the first surface of the second layer to provide capturing of particles through impaction before the flow of air proceeds to pass out of the particle collection chamber through an outlet nozzle.

The outlet nozzles may have a similar size as the inlet nozzles. However, according to an embodiment, the outlet nozzles may have a larger cross-sectional size than the inlet nozzles. Since size of the outlet nozzles does not necessarily affect the efficiency of capturing of particles, size of the outlet nozzles may be freely designed. For instance, a diameter of the outlet nozzles may typically be at least 1.5 times larger than the diameter of the inlet nozzles, such as 2 times larger.

The outlet nozzles may have identical shapes and sizes. This may facilitate that the flow of air is homogeneously distributed when passing through the collecting device. However, it should be realized that there may be varying shapes between different outlet nozzles, e.g. if it would be desired to control flow of air in a particular manner through the particle collection chamber.

According to another embodiment, the second layer does not comprise any outlet nozzles. Rather, the collecting device may comprise outlet nozzles through side walls of the particle collection chamber.

According to an embodiment, the position of the first ends of the outlet nozzles in the second layer is shifted with respect to a position of the second ends of the inlet nozzles such that a lateral distance along the first surface of the second layer between an edge of the second end of the inlet nozzle and an edge of the first end of the outlet nozzle is at least 20 μm, or is larger than a diameter of the inlet nozzle at the second end of the inlet nozzle.

This may imply that the flow of air exiting from the inlet nozzles will impact the first surface of the second layer between outlet nozzle openings in the first surface so as to ensure efficient capturing of particles.

According to an embodiment, the first layer and the second layer are spaced apart by a distance in a range of 10-150 μm, such as in a range of 20-100 μm.

In an embodiment, the first and the second layer are spaced apart by a distance smaller than a diameter of the inlet nozzles. This may advantageously be combined with the outlet nozzles being shifted with respect to the inlet nozzles such that the lateral distance is larger than the diameter of the inlet nozzles. This may further ensure that efficient capturing of particles is provided.

Although sizes are discussed above in relation to diameters, the shapes need not necessarily be circular. Similar relations in sizes may be provided also for other shapes of the inlet and outlet nozzles, such as for rectangular shapes. A size of a rectangularly shaped nozzle may be defined by the largest side of the rectangle. Similarly, sizes of other shapes of nozzles may be defined by a largest dimension of the nozzle.

According to an embodiment, the collecting device further comprises a reagent inlet for providing a liquid reagent into an analysis chamber.

As mentioned above, the particle collection chamber may form the analysis chamber. However, according to other embodiments, mechanical adjustments of the particle collection chamber may be performed for forming the analysis chamber.

According to an embodiment, the reagent inlet is provided through the first layer. The first layer may be easily accessible to receive a reagent and it may therefore be suitable to provide the reagent inlet through the first layer. The reagent inlet may be peripherally arranged in relation to the analysis chamber, such that provision of the reagent inlet through the first layer does not affect flow of air through the collection chamber or only affects flow of air to a small degree.

According to another embodiment, the reagent inlet is provided through a portion of the first layer, which may be arranged above the analysis chamber after the first layer has been slid. Thus, the reagent inlet need not provide a passage to the particle collection chamber during particle collection such that the reagent inlet does not at all affect particle collection of the collecting device.

According to yet another embodiment, the reagent inlet is provided through the second layer. This further ensures that the reagent inlet does not affect collection of particles in the particle collection chamber.

Thanks to the collecting device comprising a reagent inlet, liquid reagents may be provided into the analysis chamber for causing reactions in the analysis chamber. The reactions may for instance expose substance(s) of interest and/or provide multiplication of substance(s) to facilitate detection of presence of a substance in the flow of air.

The reagent inlet may be configured to draw a reagent through the reagent inlet by a capillary force. This may ensure that a reagent may be easily provided into the analysis chamber. For instance, a droplet of the reagent may be arranged on a surface provided with the reagent inlet in the vicinity of the reagent inlet and the capillary force may draw the reagent into the analysis chamber.

In some embodiments, the inlet nozzles or the outlet nozzles may also function as a reagent inlet.

It should be realized that in some embodiments no reagent inlet is necessary. For instance, depending on the application, there may not be a need for any reaction to take place, but rather measurements may be performed directly on the captured particles. Also, according to an embodiment, a dry reagent may be provided. In such case, the dry reagent may be provided in the analysis chamber before the particles are even collected.

According to an embodiment, the collecting device is configured to seal the analysis chamber for trapping a liquid sample in the analysis chamber.

Thanks to sealing of the analysis chamber, it may be ensured that substance(s) or particles may not escape from the analysis chamber during reactions, e.g. through evaporation.

It should be realized that the collecting device may be configured in many different manners for sealing the analysis chamber. For instance, the collecting device may be arranged to receive cap(s) for sealing nozzles and reagent inlets. However, the collecting device may alternatively be provided with features within the collecting device for sealing the analysis chamber.

It should further be realized that the collecting device need not necessarily be configured to seal the analysis chamber at all. For instance, if no reaction is to take place in the analysis chamber before measurements are performed, there may not be any need to seal the analysis chamber. On the other hand, even if a dry reagent is provided, the collecting device may still be configured to seal the analysis chamber in order to avoid evaporation from the analysis chamber.

According to an embodiment, the inlet nozzles comprise a first portion extending from the first end to a constriction arranged at the second end of the inlet nozzles, wherein the inlet nozzles has a smaller cross-sectional size in the constriction than in the first portion for forming a capillary force to maintain the liquid sample in the analysis chamber.

Thus, the inlet nozzles may be designed so as to ensure that a liquid sample is retained in the analysis chamber. This may be beneficial in that no active step may be needed for sealing the analysis chamber.

It should be realized that the outlet nozzles may be similarly shaped to have a constriction arranged at the first end of the outlet nozzles and a first portion extending from the constriction to the second end of the outlet nozzles, wherein the outlet nozzles have a smaller cross-sectional size in the constriction than in the first portion.

The inlet nozzles may be provided with a constriction in order to provide a capillary force for sealing the analysis chamber. However, it should be realized that the inlet nozzles may be provided with a constriction for other purposes. Thus, the inlet nozzles may be designed to have a constriction at the second ends in order to provide the inlet nozzles with a desired size for providing efficient capture of particles through impaction in the collecting device and/or for ensuring a desired pressure drop at a transition between the inlet nozzles and the particle collection chamber for controlling a required supply pressure of the flow of air.

According to an embodiment, the collecting device comprises valves for sealing the analysis chamber.

Thus, the collecting device may be configured to close one or more valves for sealing the analysis chamber. The valves may be mechanically or electrically controlled for closing the valves.

According to an embodiment, the inlet nozzles are configured at the second end to have a diameter in a range of 20-300 μm, such as 100-200 μm. In other embodiments, the inlet nozzles are configured at the second end to have a diameter in a range of 20-200 μm, such as 20-150 μm, such as 20-80 μm, such as 20-60 μm, such as 40-60 μm.

The size of the inlet nozzles may be chosen in relation to a desired efficiency of collection of particles, a desired size of particles to be collected, and a required supply pressure for forcing the flow of air through the collection device.

For instance, it may be desired that particles having a small diameter are to be captured. According to an embodiment, particles having a size as small as a diameter of 300 nm are to be captured. The nozzle size may thus need to be designed such that the small particles may be captured.

A size of a nozzle diameter as large as 300 μm may allow capture of particles smaller than 300 nm, but with a limited capturing efficiency and with a requirement that a relatively large supply pressure is provided by the person breathing into the collecting device in order to achieve the capturing efficiency. Thus, while a nozzle diameter up to 300 μm may provide an acceptable capturing of particles, it may be desired that the nozzle diameter is smaller than 300 μm. For instance, by decreasing the nozzle diameter to 200 μm, 150 μm or even 80 μm, the efficiency of capturing small particles (sizes smaller than 300 nm) may be higher and the requirements on the supply pressure to be provided by the person breathing into the collecting device in order to achieve a fixed capturing efficiency may be decreased. It should be realized that capturing efficiency is related to, among other, pressure drop through the collecting device, nozzle diameter and number of nozzles. Thus, in order to maintain a fixed capturing efficiency, the number of nozzles may need to be increased when the nozzle diameter is decreased, such that a flow rate of the flow of air per nozzle decreases. This may in combination result in that the required supply pressure for providing a desired flow of air through the nozzles for maintaining the fixed capturing efficiency decreases when the nozzle diameter decreases.

A size of a nozzle diameter being 20 μm may allow efficient capture of small particles while not requiring a large supply pressure to be provided for achieving the capturing efficiency. However, increasing the size of the nozzle diameter somewhat from 20 μm may not substantially change the sizes of the particles that may be efficiently captured. Thus, the size of the nozzle diameter may advantageously be larger than 20 μm, such as 40 μm or even 60 μm.

It should also be realized that by setting a larger dimension of the nozzles, fewer nozzles may need to be provided while allowing a large flow rate of air through the collecting device. Also, a larger size diameter may set more lenient requirements on tolerances in manufacturing of the collecting device.

Thus, according to an embodiment, the inlet nozzles are configured at the second end to have a diameter in a range of 20-300 μm.

According to another embodiment, the inlet nozzles are configured at the second end to have a diameter in a range of 20-200 μm.

According to another embodiment, the inlet nozzles are configured at the second end to have a diameter in a range of 20-150 μm.

According to another embodiment, the inlet nozzles are configured at the second end to have a diameter in a range of 20-80 μm.

According to another embodiment, the inlet nozzles are configured at the second end to have a diameter in a range of 20-60 μm.

According to another embodiment, the inlet nozzles are configured at the second end to have a diameter in a range of 40-60 μm.

According to an embodiment, a number of inlet nozzles is larger than 100.

The number of inlet nozzles used may control a flow rate through the collecting device. Since the inlet nozzles may need to have a small diameter size and it is desired that the supply pressure provided by the person breathing into the collecting device is relatively low, the number of inlet nozzles may need to be high in order to provide a sufficient flow rate of air through the collecting device. A sample collected through breathing may desirably be collected within a minute, as it would ensure that the sampling may be quickly performed and in order not to exhaust the person providing the sample. Thus, the flow rate through the collecting device should be sufficiently high such that a relatively large volume of air may be sampled. Therefore, the number of inlet nozzles may need to be quite large, such as more than 100. It should also be realized that with a smaller inlet nozzle diameter being used, the number of nozzles should be larger in order to maintain the total flow rate through the collecting device.

According to an embodiment, the collecting device is configured to provide a collection efficiency of at least 50% for particles having a diameter larger than 300 nm when the collecting device receives a flow of air having a pressure in a range of 10-30 mbar.

The collecting device may thus be designed in relation to receive a flow of air having a pressure in a range of 10-30 mbar. Such supplied pressure may easily or relatively easily be provided by the person breathing into the collecting device. Thus, the collecting device may be designed with a size of inlet nozzles and arrangement of inlet nozzles in relation to the particle collection chamber in order to ensure that the collection efficiency is at least 50% for particles as small as having a diameter of 300 nm.

According to an embodiment, the collecting device further comprises at least one contact arranged on the first or the second layer for receiving energy to provide heating to a liquid sample in an analysis chamber.

As mentioned above, the particle collection chamber may form the analysis chamber. However, according to other embodiments, mechanical adjustments of the particle collection chamber may be performed for forming the analysis chamber.

Thanks to the collecting device being able to provide heating of the liquid sample, thermal energy may be provided which may control a reaction in the analysis chamber.

In some embodiments, thermal energy may be cyclically provided such that the liquid sample is subject to several cycles of heating and cooling for controlling a desired reaction in the analysis chamber.

According to an embodiment, the collecting device is configured for receiving a liquid reagent to be mixed with the collected particles in an analysis chamber, receiving heat for thermal lysis to expose RNA of severe acute respiratory syndrome coronavirus 2 (SARS-CoV-2) in the collected particles, converting the RNA to DNA using reverse transcriptase based on the reagent in the analysis chamber and providing thermal cycling for amplification of the DNA using quantitative polymerase chain reaction.

As mentioned above, the particle collection chamber may form the analysis chamber. However, according to other embodiments, mechanical adjustments of the particle collection chamber may be performed for forming the analysis chamber.

Thus, the collecting device may be configured to enable amplification of presence of SARS-CoV-2 within an analysis chamber which is provided with collected particles from a person breathing through a collecting device. In this manner, the collecting device may facilitate obtaining accurate and very quick results of presence of SARS-CoV-2 for identifying people infected by the disease so as to enable reducing spreading of the disease.

According to a second aspect, there is provided a sample collector comprising: the collecting device according to the first aspect; a mouthpiece for receiving a flow of air from exhalation by a human being; wherein the collecting device is arranged in the sample collector to receive the flow of air from the mouthpiece.

Effects and features of this second aspect are largely analogous to those described above in connection with the first aspect. Embodiments mentioned in relation to the first aspect are largely compatible with the second aspect.

The sample collector may provide a suitable form factor for collecting samples through self-test by persons. The sample collector may comprise a mouthpiece for allowing the human being to breathe normally or blow into the sample collector for providing a sample. Hence, the sample collector may be easily and intuitively used. Further, the collecting device may be arranged within the sample collector such that the flow of air is guided through the collecting device for ensuring that the flow of air provided by the human being passes through the collecting device wherein particles may be collected with a high efficiency.

The sample collector may be disposable, since the sample collector may potentially carry viral particles after a sample has been provided. Therefore, the sample collector may be relatively simple. Analysis of the collected particles may therefore be performed by an instrument and the sample collector may be configured to fit being placed in the instrument wherein the analysis is made.

According to an embodiment, the sample collector further comprises a flow meter for providing a measure of a volume of air being provided through the mouthpiece.

Thus, the sample collector may thanks to the flow meter determine when a sufficient volume of air has been passed through the collecting device for allowing a robust measurement to be made.

The sample collector may further comprise an indicator for outputting information to a user that a sufficient volume of air has been provided into the sample collector. For instance, the sample collector may comprise a loudspeaker for outputting a sound or a lamp for outputting a light signal to indicate to the user when a sufficient volume of air has been provided.

According to an embodiment, at least a portion of a wall of the sample collector is transparent or translucent for enabling analysis of airborne particles in the analysis chamber of the collecting device by a measurement based on light through the transparent or translucent portion of the wall of the sample collector.

Thus, the measurement based on light may be performed from a position external to the sample collector. This implies that the sample collector need not be mechanically manipulated in an analysis instrument in order to perform measurements.

It should be realized that analysis may be performed in other manners on the collecting device, without requiring that the collecting device is removed from the sample collector. For instance, the sample collector may be provided with hole(s) in a wall of the sample collector to allow a waveguide or optical fiber to be inserted into the sample collector such that illumination of a sample in the analysis chamber and capturing of light from the sample may be achieved while the collecting device is arranged in the sample collector.

As mentioned above, it may be beneficial that analysis of a sample in the collecting device is performed while the collecting device is maintained in the sample collector. Thus, the sample collector may further be provided with interfaces for ensuring that any functions that need to be performed for preparing the sample for analysis may be provided from the analysis instrument without requiring the collecting device to be removed from the sample collector. Alternatively, the sample collector may be provided with internal components for providing such functions that need to be performed for preparing the sample for analysis from within the sample collector.

However, it should also be realized that in some embodiments, an analysis instrument may be configured for mechanically removing the collecting device from the sample collector so as to allow access to the collecting device within the analysis instrument. Thus, while the removal of the collecting device from the sample collector may be complicated, functions that need to be performed for preparing the sample for analysis may be relatively easily provided within the analysis instrument.

According to an embodiment, the sample collector may be provided with a reagent connection for receiving a liquid reagent to the analysis chamber of the collecting device. For instance, the reagent connection may be provided with a hole in a wall of the sample collector through which a syringe or another device carrying a channel for providing a liquid reagent may be extended. The syringe may thus be arranged through the hole and guided by the hole to provide a tip of the syringe close to the reagent inlet of the collecting device. A droplet of liquid reagent provided by the syringe may thus land on a surface of the collecting device and be drawn by a capillary force into the reagent inlet and further to the analysis chamber of the collecting device.

Thus, it is conceivable that the liquid reagent may be provided to the collecting device while arranged in the sample collector from an analysis instrument, such that no reagent may need to be stored on the sample collector. However, it should also be realized that in other embodiments, the reagent may be stored in the sample collector, which may facilitate a less complex interface between the sample collector and the analysis instrument in which it is placed.

According to an embodiment, the sample collector may be provided with a heat source for providing thermal energy to the contact of the collecting device. Thus, the heat source may be provided within the sample collector such that there may be no need to provide a connection to an external heat source in the analysis instrument, when thermal energy is to be provided to the analysis chamber of the collecting device while the collecting device is arranged in the sample collector. The analysis instrument may be configured to provide a control signal for controlling timing of thermal energy being provided to the contact of the collecting device. According to another embodiment, the sample collector comprises a heat connection for enabling a heat source of the analysis instrument to be connected to the contact of the collecting device. The heat connection may for instance be a wire extending from a wall of the sample collector to the contact of the collecting device.

According to a third aspect, there is provided an analysis instrument for analysis of particles in a human breath, said analysis instrument comprising: a holder defining a plurality of receiving positions for receiving a plurality of sample collectors according to the second aspect; a plurality of analysis units, wherein one analysis unit is associated with each receiving position, wherein each analysis unit comprises a light source for illuminating a sample in the analysis chamber of the collecting device of the sample collector, and a light detector for detecting light from the sample; and a processing unit for processing a signal from the light detector for analyzing the sample.

Effects and features of this third aspect are largely analogous to those described above in connection with the first and second aspects. Embodiments mentioned in relation to the first and second aspects are largely compatible with the third aspect.

The analysis instrument may thus enable analysis to be performed for several sample collectors in parallel. With a test that may be quickly performed, such as within 5 minutes from being provided to the analysis instrument, a high throughput of test results may be provided by the analysis instrument. This implies that the analysis instrument may be suitable for being placed at a point that is passed by many people for screening people at such a point. For instance, the analysis instrument may be suitable for being placed at an entrance to an airport, a shop, or a company facility, for screening people before admitting people through the entrance. The high throughput of the analysis instrument may allow such screening to be performed without long queues being formed.

Thanks to the analysis instrument comprising a plurality of analysis units, analyses of plural samples in different sample collectors may be performed in parallel. It should be realized that some parts of analysis units may still be shared. For instance, the analysis instrument may comprise a storage of reagent, in which a liquid reagent may be cooled in order to enable long-term storing of the reagent. The analysis instrument may comprise a single reagent storage and may comprise conduits for transporting reagent from the reagent storage to each of the analysis units associated with a receiving position.

The analysis instrument may comprise a single processing unit which is configured to receive measurements in the form of signals from a light detector for analyzing the sample. The single processing unit may thus receive measurements from all of the analysis units so as to support processing of the measurements for all analysis units. However, it should be realized that the analysis instrument may alternatively comprise a plurality of processing units, wherein each processing unit may be dedicated to a particular analysis unit. This may facilitate parallel processing of measurements and may improve throughput of providing analysis results by the analysis instruments, even though the processing time may be only a small fraction of the time for analysis of a sample (which includes e.g. ensuring that the sample is subject to reactions with a reagent).

The analysis of a sample may be based e.g. on fluorescence. Thus, a presence of a particle or a substance in the sample may be detected based on whether a sufficiently high intensity of fluorescent light may be detected by the light detector or not. In this regard, the processing of the signal from the light detector may comprise comparing an amount of detected light to a threshold. However, it should be realized that the processing by the processing unit may be much more complicated, such as analyzing a morphology of an image of a particle obtained by the light detector.

According to an embodiment, the analysis instrument is configured to transport the sample collector to a waste bin after analysis of the sample.

Thus, the analysis instrument may automatically remove sample collectors after an analysis has been performed. This implies that no manual handling of sample collectors may be needed after the sample collector has been placed in the receiving position.

For instance, a receiving position may be provided with a lid leading to a passageway from the receiving position to the waste bin, such that the lid may be opened to transport the sample collector away from the receiving position when the analysis has been performed.

According to an embodiment, the analysis instrument further comprises a user interface for identification of a user, wherein the user interface is configured to allow for touch-less input by the user.

In order to avoid that a disease is spread by people being in contact with the analysis instrument, the analysis instrument may be configured for touch-less input.

The user interface may for instance comprise a reader for reading a code, such that a user may by means of a smartphone or another device present a QR-code or another code to the reader.

The user interface may alternatively be a tag reader, which may be configured to read an individual tag, which may identify a user. For instance, at a company facility, employees may anyway wear an individual tag based e.g. on radio-frequency identification (RFID) technology, and such tags may be used for identifying a user through the touch-less input to the analysis instrument.

According to an embodiment, the analysis instrument further comprises a communication unit for communicating a result of analysis of the sample to a remote unit specified by a user.

Thus, the user may receive the analysis result directly to a specified remote unit. This may enable analysis results to be provided directly to a phone of the user, such that the user may have immediate access to the analysis result. For instance, a user may not be admitted through an entrance before the user may show a negative analysis result, i.e. that the user is not infected.

According to a fourth aspect, there is provided a method for collection of particles for analysis, said method comprising: passing a flow of air carrying airborne particles through a plurality of inlet nozzles through a first layer of a collecting device for passing the flow of air from the inlet nozzles into a particle collection chamber, wherein the particle collection chamber has a first and a second side defined by the first layer and a second layer, respectively; and capturing airborne particles through impaction in the particle collection chamber by the flow of air being passed into the particle collection chamber impinging on a first surface of the second layer facing the first layer in the particle collection chamber; wherein the particle collection chamber provides optical access for performing a measurement, based on light, of airborne particles collected in the particle collection chamber at a first measurement position arranged such that the second layer is between the second side of the particle collection chamber and the first measurement position or at a second measurement position, which is arranged at an opposite side to the first measurement position in relation to the second side of the particle collection chamber.

Effects and features of this fourth aspect are largely analogous to those described above in connection with the first, second, and third aspects. Embodiments mentioned in relation to the first, second, and third aspects are largely compatible with the fourth aspect.

Thanks to the method, an efficient capturing of airborne particles may be provided in a particle collection chamber. The plurality of inlet nozzles may be designed so as to provide a high impaction capturing efficiency. Further, thanks to the flow of air being provided through a plurality of inlet nozzles, the method facilitates providing a flow of air through the inlet nozzles of the collecting device without requiring a high supply pressure to be provided by the person breathing through the collecting device.

The method thus enables capturing of particles in a particle collection chamber in an efficient manner so as to ensure that particles captured on the particle collection chamber may be analyzed e.g. for determining presence of a substance. The method provides a sample collection of particles from a human being so as to highly reduce discomfort in the sample collection compared e.g. to a sample being collected by a nasal or throat swab.

The collected particles may be directly analyzed while being arranged on the first surface of the second layer. Thus, the sample may be directly analyzed and there may be no need to move the collected particles for analysis. The collected particles may however undergo one or more steps of reactions while being arranged on the first surface of the second layer before a measurement based on light for analyzing the collected particles is made.

According to a fifth aspect, there is provided a method for analysis of samples of particles in human breath; said method comprising: receiving a plurality of sample collectors in a plurality of receiving positions of an analysis instrument, wherein each sample collector comprises a collecting device carrying a sample of airborne particles being captured in an analysis chamber in the collecting device by impaction therein; performing measurements based on light in each of the receiving positions, wherein a light detector detects light from the sample in the analysis chamber while the collecting device is arranged in the sample collector; and processing a signal form the light detector for analyzing the sample.

Effects and features of this fifth aspect are largely analogous to those described above in connection with the first, second, third, and fourth aspects. Embodiments mentioned in relation to the first, second, third, and fourth aspects are largely compatible with the fifth aspect.

Thanks to the method a sample in a collecting device may be analyzed without requiring the collecting device to be removed from a sample collector in which the collecting device is arranged during collecting of a sample. This ensures that handling of sample collectors is simple in an analysis instrument and may also ensure that analysis may be quickly performed.

Thanks to sample collectors being received in a plurality of receiving positions in the analysis instruments, measurements may be performed in parallel so as to provide a high throughput of analysis results from the analysis instrument.

According to an embodiment, the method further comprises, before performing measurements, introducing a liquid reagent in the analysis chamber, while the collecting device is arranged in the sample collector.

Thus, a liquid reagent may be provided for causing a desired reaction in the analysis chamber. Thanks to the method being arranged to introduce the liquid reagent while the collecting device is arranged in the sample collector, the method allows analysis involving provision of liquid reagents while the collecting device is arranged in the sample collector.

According to an embodiment, the method further comprises, before performing measurements and after introducing a liquid reagent, providing thermal energy to the analysis chamber, while the collecting device is arranged in the sample collector, for controlling a reaction in the analysis chamber.

Thanks to providing thermal energy, a reaction in the analysis chamber may be controlled such that a desired reaction in the analysis chamber may be induced.

According to an embodiment, the thermal energy is provided for thermal lysis to expose RNA of severe acute respiratory syndrome coronavirus 2 (SARS-CoV-2) in the captured particles, converting the RNA to DNA using reverse transcriptase based on the reagent in the analysis chamber and providing thermal cycling for amplification of the DNA using quantitative polymerase chain reaction.

Thus, the method may be suited for amplifying presence of SARS-CoV-2 so as to allow accurate detection of presence of SARS-CoV-2 in a sample with a very fast analysis result while allowing the sample to be captured in a manner causing no or very little discomfort to the person providing the sample.

According to a sixth aspect, there is provided a collecting device for collection of airborne particles from a flow of air, said collecting device comprising: a first layer and a second layer, wherein the first layer and the second layer are arranged to be spaced apart for forming a particle collection chamber between the first and the second layer, wherein the first layer comprises a plurality of inlets configured to extend through the first layer for transporting the flow of air therethrough into the particle collection chamber; wherein ends of the inlets are configured to face a first surface of the second layer for capturing airborne particles in the flow of air entering the particle collection chamber through the ends of the inlets by impaction of airborne particles on the first surface of the second layer; wherein the second layer comprises a plurality of outlets configured to extend through the second layer for transporting the flow of air therethrough out of the particle collection chamber; wherein the inlets and outlets are staggered such that the center axes of the inlets are displaced from the center axes of the outlets; wherein the collecting device is configured such that the flow of air experiences a pressure drop when passing the collecting device, the pressure drop being lower than 3 kPa at a flow rate of 0.5 liters per second.

Effects and features of this sixth aspect are largely analogous to those described above in connection with the first, second, third, fourth, and fifth aspects. Embodiments mentioned in relation to the first, second, third, fourth, and fifth aspects are largely compatible with the sixth aspect. Also, embodiments of the sixth aspect may be combined with the features of any of the first, second, third, fourth, and fifth aspects.

According to an embodiment of the sixth aspect, a volume of the particle collection chamber is smaller than 30 μl, such as smaller than 20 μl.

According to an embodiment of the sixth aspect that may be combined with the features of any of the above embodiments of the sixth aspect, the collecting device is configured such the pressure drop experienced by the flow of air when passing the collecting device is lower than 1.5 kPa at a flow rate of 0.5 liters per second.

According to an embodiment of the sixth aspect that may be combined with the features of any of the above embodiments of the sixth aspect, the collecting device is configured to provide a collection efficiency of at least 50% for particles having a diameter larger than 300 nm when the collecting device receives a flow of air with a flow rate of 0.5 liters per second.

According to an embodiment of the sixth aspect that may be combined with the features of any of the above embodiments of the sixth aspect, a smallest dimension of a cross-section of the inlets is in a range of 20-300 μm, such as in a range of 100-200 μm.

It should be realized that the pressure drop experienced by the flow of air passing through the collecting device is mostly dependent on the smallest dimension of the cross-section of the inlet. Further, the collection efficiency of the particles need not be greatly impaired by a largest dimension of the cross-section of the inlet being substantially larger than the smallest dimension. For instance, the inlets may be designed as rectangular slits having a very large length and a small width, wherein the width is in the range of 20-300 μm, such as in the range of 100-200 μm. Use of rectangular slits may allow for an efficient arrangement of the inlets and outlets such that a small footprint (area of the first and/or second layer) of the collecting device may be achieved.

According to an embodiment of the sixth aspect that may be combined with the features of any of the above embodiments of the sixth aspect, a number of inlets is larger than 100, such as larger than 500, such as 1000-2000 inlets.

According to an embodiment of the sixth aspect that may be combined with the features of any of the above embodiments of the sixth aspect, a length of the inlets is in a range of 20-500 μm, such as in a range of 50-300 μm.

According to an embodiment of the sixth aspect that may be combined with the features of any of the above embodiments of the sixth aspect, a cross-section of the inlets is circular or rectangular.

According to an embodiment of the sixth aspect that may be combined with the features of any of the above embodiments of the sixth aspect, a smallest dimension of a cross-section of the outlets is in a range of 20-400 μm, such as in a range of 100-300 μm.

According to an embodiment of the sixth aspect that may be combined with the features of any of the above embodiments of the sixth aspect, a number of outlets is larger than 100, such as larger than 500, such as 1000-2000 outlets.

According to an embodiment of the sixth aspect that may be combined with the features of any of the above embodiments of the sixth aspect, a length of the outlets is in a range of 20-500 μm, such as in a range of 100-300 μm.

According to an embodiment of the sixth aspect that may be combined with the features of any of the above embodiments of the sixth aspect, wherein the first layer and the second layer are spaced apart by a gap in a range of 10-150 μm, such as in a range of 20-100 μm.

According to an embodiment of the sixth aspect that may be combined with the features of any of the above embodiments of the sixth aspect, a projection of the inlets onto the first surface of the second layer form a hexagonal arrangement of the inlets surrounding each outlet.

According to an embodiment of the sixth aspect that may be combined with the features of any of the above embodiments of the sixth aspect, a projection of an inlet onto the first surface of the second layer is configured not to overlap with a closest neighbor outlet, such as a lateral separation of an edge of the projection of the inlet to an edge of the closest neighbor outlet being at least 20 μm.

According to a seventh aspect, there is provided a method for collection of airborne particles from a flow of air, said method comprising: receiving a flow of air onto a first layer of a collecting device, wherein the first layer comprises a plurality of inlets extending through the first layer; passing the flow of air through the inlets into a particle collection chamber between the first layer and a second layer of the collecting device spaced apart from the first layer; capturing airborne particles in the flow of air entering the particle collection chamber by impaction of airborne particles on a first surface of the second layer, wherein ends of the inlets are configured to face the first surface of the second layer; passing the flow of air out of the particle collection chamber through outlets extending through the second layer of the collecting device; wherein the inlets and outlets are staggered such that the center axes of the inlets are displaced from the center axes of the outlets; wherein the collecting device is configured such that the flow of air experiences a pressure drop when passing the collecting device, the pressure drop being lower than 3 kPa at a flow rate of 0.5 liters per second.

Effects and features of this seventh aspect are largely analogous to those described above in connection with the first, second, third, fourth, fifth, and sixth aspects. Embodiments mentioned in relation to the first, second, third, fourth, fifth, and sixth aspects are largely compatible with the seventh aspect. Also, embodiments of the seventh aspect may be combined with the features of any of the first, second, third, fourth, fifth, and sixth aspects.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1A:
FIG. 1*a* is a schematic view illustrating capturing of a sample using a sample collector according to an embodiment.
Figure 1B:
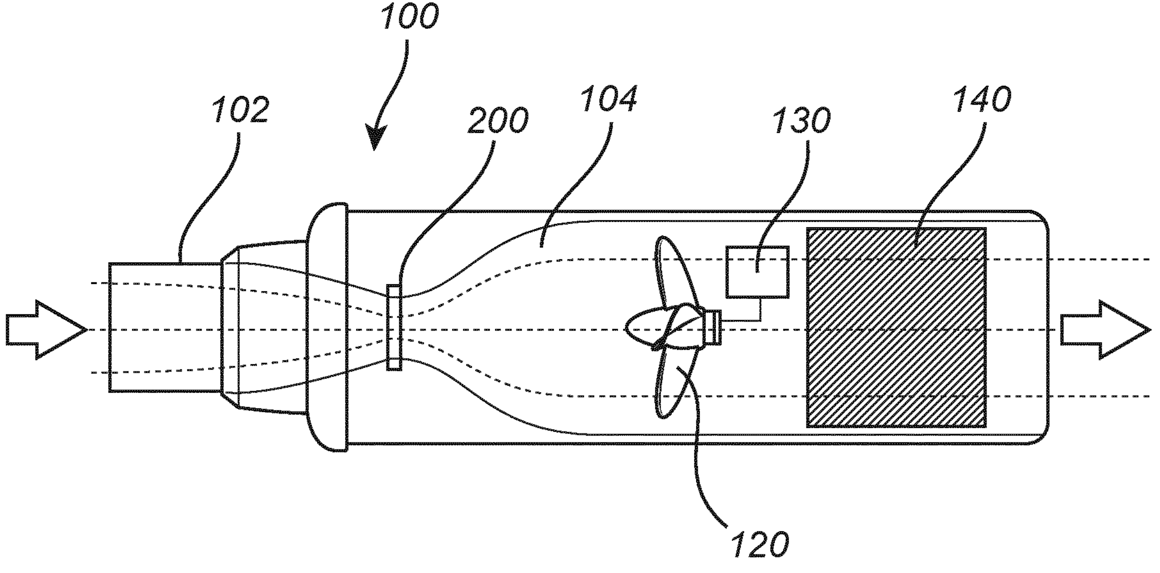
FIG. 1*b* is a schematic cross-sectional view of the sample collector.

Referring now to FIGS. 1*a*-*b*, a sample collector 100 will be described. The sample collector 100 is configured for enabling capturing of a sample based on an exhaled breath by a person, as illustrated in FIG. 1*a*.

The sample collector 100 may be used for capturing airborne particles, such as aerosols and/or droplets in the flow of air exhaled by the person. Thanks to capturing airborne particles, analysis of the airborne particles in the exhaled breath may be performed. This may be used for determining whether the person carries a disease, which is spread through droplets and aerosols produced during normal breathing, talking, coughing and sneezing. For instance, the capturing of airborne particles using the sample collector 100 may be used for screening whether a person is infected by influenza or severe acute respiratory syndrome coronavirus 2 (SARS-CoV-2). Thanks to the sample collector 100 capturing a sample based on an exhaled breath, the capturing of a sample from a person may be performed with minimal discomfort to the person.

The sample collector 100 may comprise a mouthpiece 102 to be inserted into the mouth of the person and through which the person exhales to provide a flow of air 104 through the sample collector 102.

The flow of air 104 may be guided through the sample collector 102 so as to pass a collecting device 200. The collecting device 200 will be described in further detail below. The collecting device 200 is configured to capture airborne particles from the flow of air 104 through impaction in a particle collection chamber of the collecting device 200. The collecting device 200 may be configured to capture airborne particles with high efficiency and may further allow analysis of the collected airborne particles on a surface of the particle collection chamber on which the airborne particles are captured. Furthermore, analysis of the collected airborne particles may be performed while the collecting device 200 is maintained in the sample collector 100. This implies that no manipulation of the sample collector 100 may be needed in an analysis instrument. This may imply that the analysis instrument does not need complicated mechanical components for manipulating the sample collector 100 and further a risk of spreading of disease by opening of the sample collector 100 may be avoided.

The sample collector 100 may thus be configured to be arranged in a receiving position of an analysis instrument for allowing analysis of the collected particles in the collecting device 200 of the sample collector 100 to be performed in the receiving position. Analysis performed by the analysis instrument will be described in further detail below.

The sample collector 100 may further comprise a flow meter 120. The flow meter 120 may measure the flow of air 104 so as to determine a volume of air being exhaled through the sample collector 100. The sample collector 100 may have a setting for a minimum volume of air to be provided in order to allow a reliable test result to be provided based on the captured sample. Thus, the flow meter 120 may measure the volume of air, such that the flow meter 120 may ensure that the minimum volume of air passes through the collecting device 200 in the sample collector 100.

The flow meter 120 may be connected to a control unit 130 in the sample collector 100. The control unit 130 may receive measurements from the flow meter 120 and may be configured to determine when the minimum volume of air has passed through the collecting device 200.

The sample collector 100 may further comprise an indicator (not shown), which may provide an output to the person. The control unit 130 may control the indicator to be activated when the control unit 130 determines that the minimum volume of air has passed through the collecting device 200. The indicator may for instance be a loudspeaker for outputting a sound signal or a lamp for outputting a light signal. Thus, the sample collector 100 may indicate to the person when a sufficient volume of air has been provided through the sample collector 100.

The sample collector 100 may further comprise a filter 140 through which the flow of air 104 is passed before the flow of air 104 is allowed to escape the sample collector 100. The filter 140 may be configured to capture airborne particles so as to prevent any aerosols or droplets that may potentially carry a disease to escape the sample collector 100 during capturing of a sample.

The control unit 130 may be implemented as a general-purpose processing unit, such as a central processing unit (CPU), which may execute the instructions of one or more computer programs in order to implement the functionality of the control unit 130. The control unit 130 may alternatively be implemented as firmware arranged e.g. in an embedded system, or as a special-purpose circuitry for providing only specific logical operations. Thus, the control unit 130 may be provided in the form of an ASIC or FPGA.

The control unit 130 may further comprise a non-volatile memory. The memory may store application(s), which may be loaded into a working memory of the control unit 130 for controlling the processing performed by the control unit 130.

The control unit 130 may further be configured to be connected to the collecting device 200 for providing control of functions to be performed during analysis of a sample while the sample collector 100 is arranged in an analysis instrument. The control unit 130 may thus be configured to communicate with the analysis instrument, e.g. via wired connection or via a wireless communication unit, in order for the control unit 130 to receive control signals from the analysis instrument.

Further below, the analysis instrument and relations between the analysis instrument and the sample collector 100 will be described in more detail.

Figure 2:
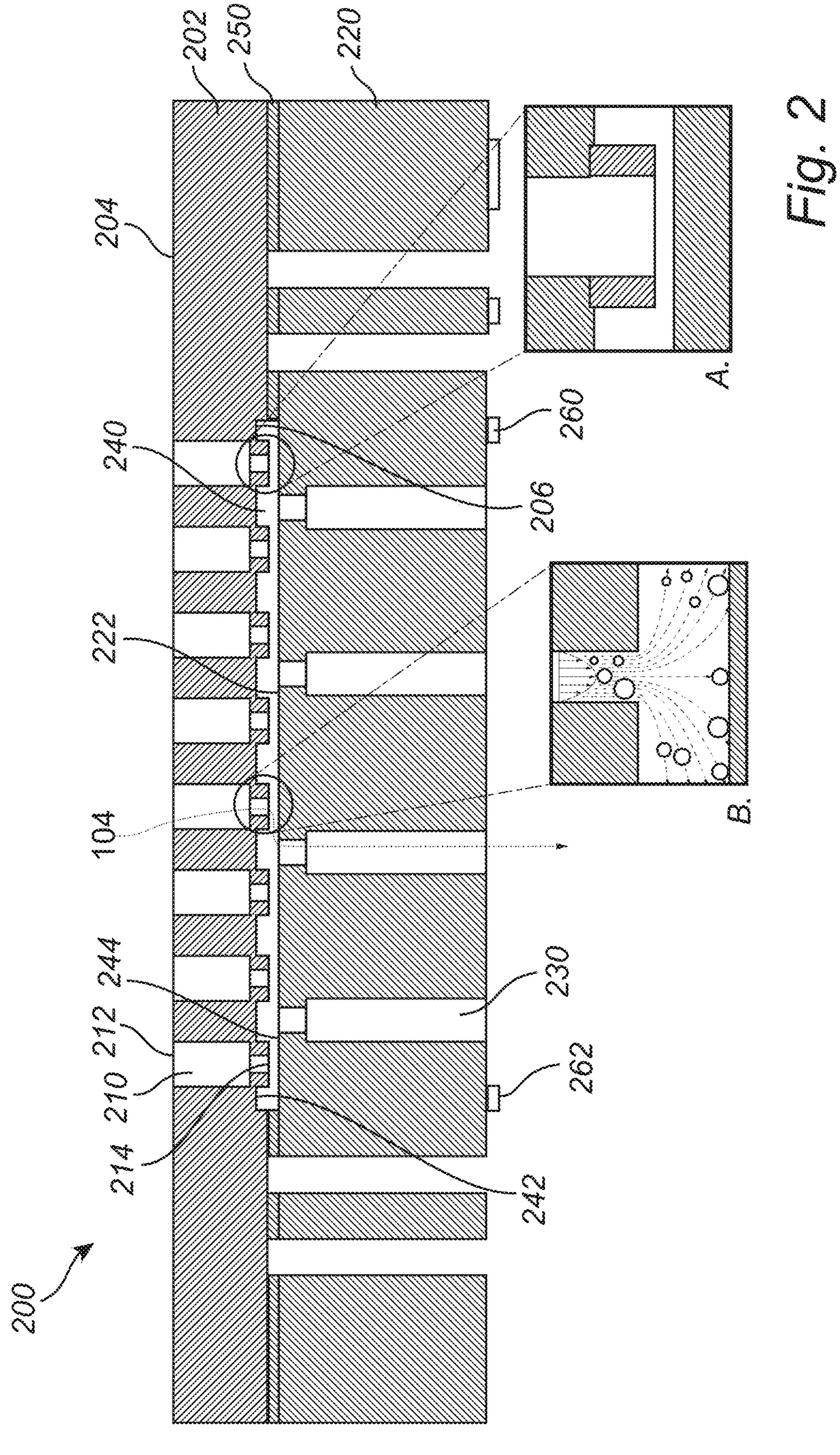
FIG. 2 is a schematic cross-sectional view of a collecting device according to an embodiment.

Referring now to FIG. 2, the collecting device 200 will be further described. The collecting device 200 may be arranged in the sample collector 100 which provides an interface for allowing a flow of air from a human being to be provided through the collecting device 200. However, it should be realized that the collecting device 200 may be arranged to receive the flow of air in different manners and need not necessarily be mounted in a sample collector 100 or any other apparatus.

The collecting device 200 may comprise a first layer 202 and a second layer 220. The first layer 202 and the second layer 220 may be spaced apart for defining a particle collection chamber 240 between the first layer 202 and the second layer 220.

The first layer 202 comprises a first surface 204 configured to receive the flow of air 104 in the sample collector 100 and a second surface 206 facing the second layer 220. The first layer 202 further comprises a plurality of inlet nozzles 210 having a first end 212 at the first surface 204 of the first layer 202 and a second end 214 at the second surface 206 of the first layer 204.

The inlet nozzles 210 are configured to extend through the first layer 202 for transporting the flow of air 104 through the first layer 202 from the first end 212 to the second end 214. The second ends 214 of the inlet nozzles 210 are configured to face a first surface 222 of the second layer 220. Thus, when the flow of air 104 passes through the inlet nozzles 210, the flow of air 104 will impinge on the first surface 222 of the second layer 220 such that airborne particles may be collected on the first surface 222 of the second layer 220 and, hence, in the particle collection chamber 240, by impaction.

The particle collection chamber 240 has a first side 242 and a second side 244, wherein the first side 242 is defined by the second surface 206 of the first layer 204 and the second side 244 is defined by the first surface 222 of the second layer 220. The particle collection chamber 240 may further be defined by side surfaces formed in a spacer material 250 between the first layer 202 and the second layer 220.

As shown in the enlarged insert A, the inlet nozzles 210 may be configured to extend to protrude from second surface 206 of the first layer 202 to extend further into the particle collection chamber 240. This may imply that the second ends 214 of the inlet nozzles 210 are closer to the first surface 222 of the second layer 220 so as to improve capturing of particles by impaction while ensuring that a volume of the particle collection chamber 240 is not too small.

The collecting device 200 is configured to provide optical access for performing a measurement, based on light, of airborne particles collected in the particle collection chamber 240.

The measurement may be performed at a first measurement position, arranged below the particle collection chamber 240 in the orientation shown in FIG. 2. The measurement may in the first measurement position be performed through the second layer 220, which may thus be transparent or translucent to provide the optical access to the collected particles on the first surface 222 of the second layer 220.

The measurement may alternatively be performed at a second measurement position, opposite to the first measurement position. The second measurement position is thus above the particle collection chamber 240 in the orientation shown in FIG. 2. The measurement may in the second measurement position be performed through the first layer 202, which may thus be transparent or translucent to provide the optical access to the collected particles on the first surface 222 of the second layer 220.

However, according to an embodiment, the first layer 202 may be removable and may be replaced by a substitute layer for defining an analysis chamber between the substitute layer and the second layer 220. Thus, the second measurement position may be arranged such that the substitute layer is between the second measurement position and the first surface 222 of the second layer 220 on which the particles are collected. According to yet another embodiment, measurements may be performed directly on the collected particles, without first subjecting the collected particles to any reactions. In such case, the first layer 202 may be removed and the measurement may be performed on the exposed first surface 222 of the second layer 220.

According to an embodiment, which will be discussed below, the first layer 202 is not removed after particle collection. Rather, the particle collection chamber 240 also forms an analysis chamber 240 in which reactions may take place before measurements are performed on the collected particles in the analysis chamber 240.

As shown in the enlarged insert B, airborne particles may be captured by impaction on the first surface 222 of the second layer 220, before the flow of air 104 proceeds to outlet nozzle 230 extending through the second layer 220. The outlet nozzles 230 may be configured for transporting the flow of air 104 through the second layer 220 such that the flow of air 104 may pass through the collecting device 200 through the inlet nozzles 210, along the first surface 222 of the second layer 220 and then through the outlet nozzles 230.

Figure 3:
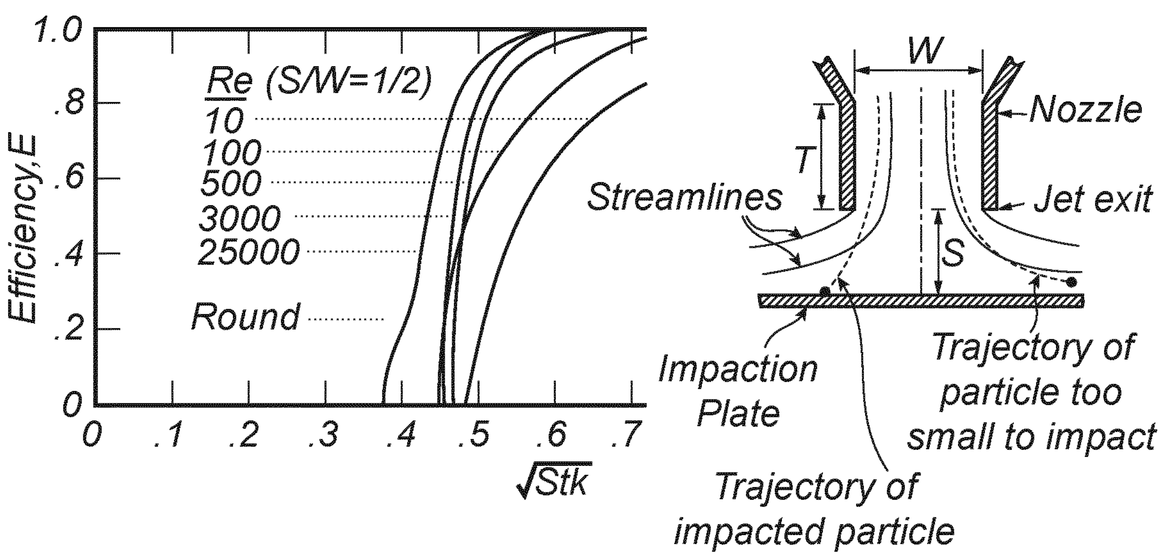
FIG. 3 is a graph defining efficiency of capturing of particles through impaction and an explanatory cross-section of an inlet nozzle providing air flow for capturing particles through impaction.

Referring now to FIG. 3, design of the collecting device 200 for providing an efficient capturing of particles will be discussed.

FIG. 3 is based on a figure from Marple and Willeke, "Impactor Design", Atmospheric Environment, vol. 10 (10), 1976, pp. 891-896.

The collection efficiency, the percentage of particles that will impact the plate, is a strong function of the Stokes number and Reynolds number. The Stokes number is defined as:

$$Stk = \frac{4\rho_p Q C_c d_p^2}{9\pi N \mu_g W^3}$$

where $\rho_p$ is the density of the particle, Q is the total volumetric flow rate for an array of inlet nozzles, $C_c$ is the Cunningham correction factor (taken as 1 for all subsequent calculations), $d_p$ is the particle diameter, N is the number of nozzles in the array, $\mu_g$ is the dynamic viscosity of air, and W is the nozzle diameter. For the above study, distances T and S as indicated in FIG. 3 are T=2W and S=W/2. The Reynolds number is defined as:

$$Re = \frac{4\rho_p Q}{\pi N \mu_g W}$$

According to the FIG. 3, in order to capture 50% of the particles at a Reynolds number of Re=100, then $$\sqrt{\frac{4\rho_p Q C_c d_p^2}{9\pi N \mu_g W^3}} \approx 0.48.$$

Note that for increasing particle diameters, $\sqrt{Stk}$ increases and higher collection efficiencies are obtained. Conversely, small particles are more difficult to capture than large particles.

The collecting device 200 is intended to be used for collecting a sample from exhaled breath from a person and then perform subsequent analysis on the collecting device 200 to screen for possible infectious disease(s). The analysis, for instance, could be end-point or quantitative reverse transcriptase polymerase chain reaction (RT-PCR) for an RNA virus like SARS-CoV-2.

It is desired to have a high collection efficiency of approximately 50% for particle diameters down to 300 nm. This is to ensure that enough sample can be collected to have reasonably sensitive results for detection of the biological agent of interest from a reasonably small sampling of exhaled breath from the patient.

Furthermore, it is intended that the person exhales through the collecting device 200. This places stringent requirements on the supply pressure and flow rate that the collecting device 200 should handle. For instance, a reasonably comfortable pressure by the person is less than 30 mbars at an exhaled flow rate less than 40 liters/min or less than 30 liters/min.

Figure 4:
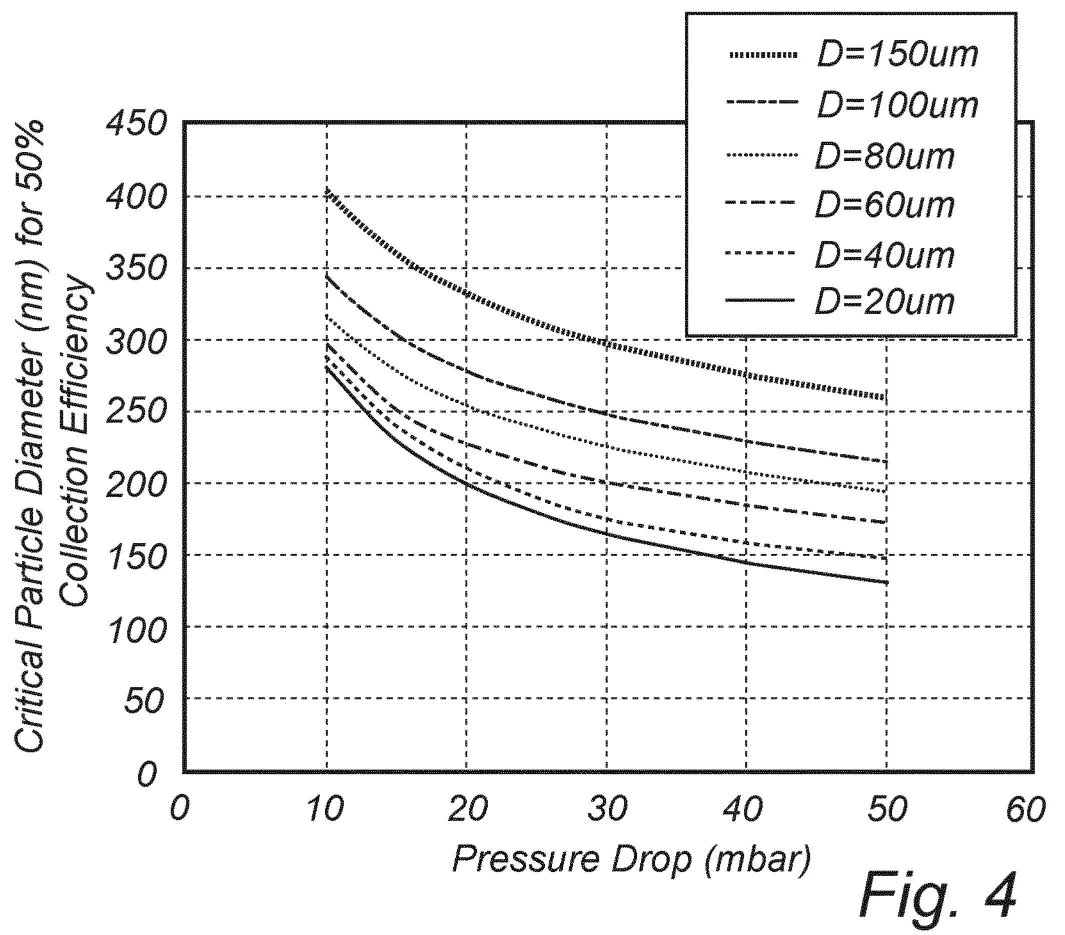
FIG. 4 is a graph illustrating a relation between diameter size of a particle that is efficiently captured, diameter size of an inlet nozzle and pressure drop provided by supplied pressure of air flow.
Figure 5:
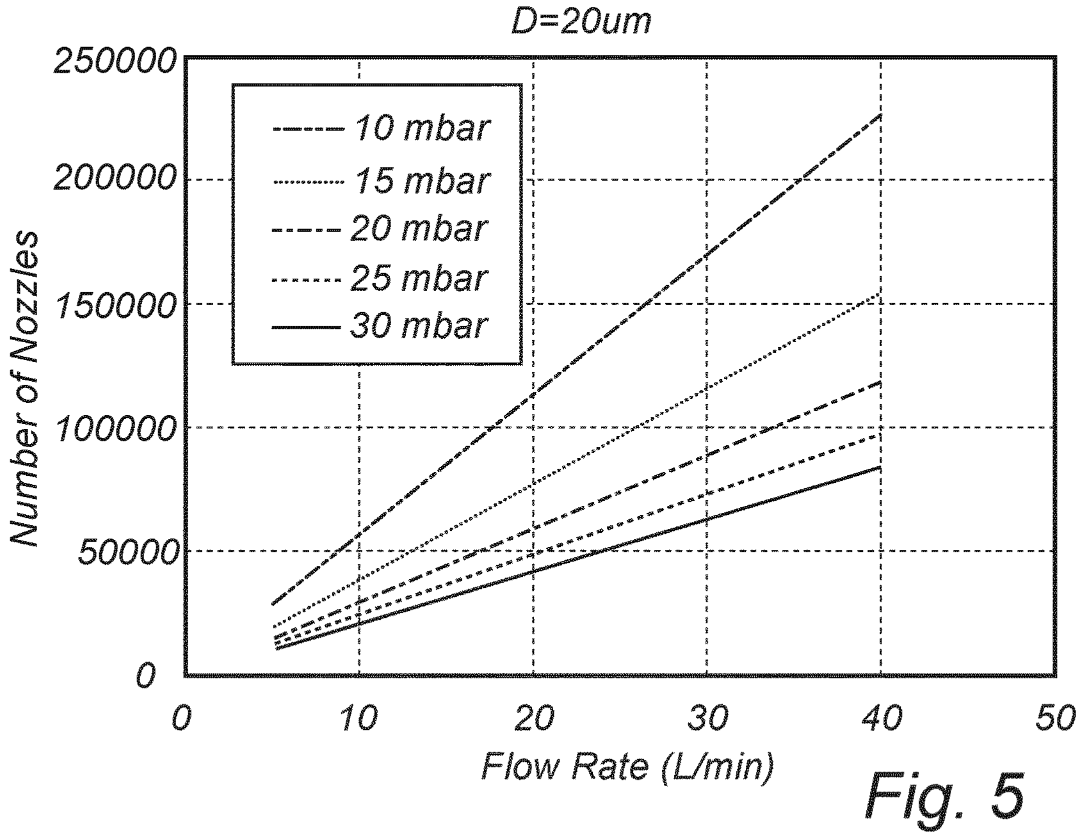
FIGS. 5-10 are graphs illustrating relations between number of nozzles, pressure drop and flow rate for varying diameter sizes of inlet nozzles.
Figure 6:
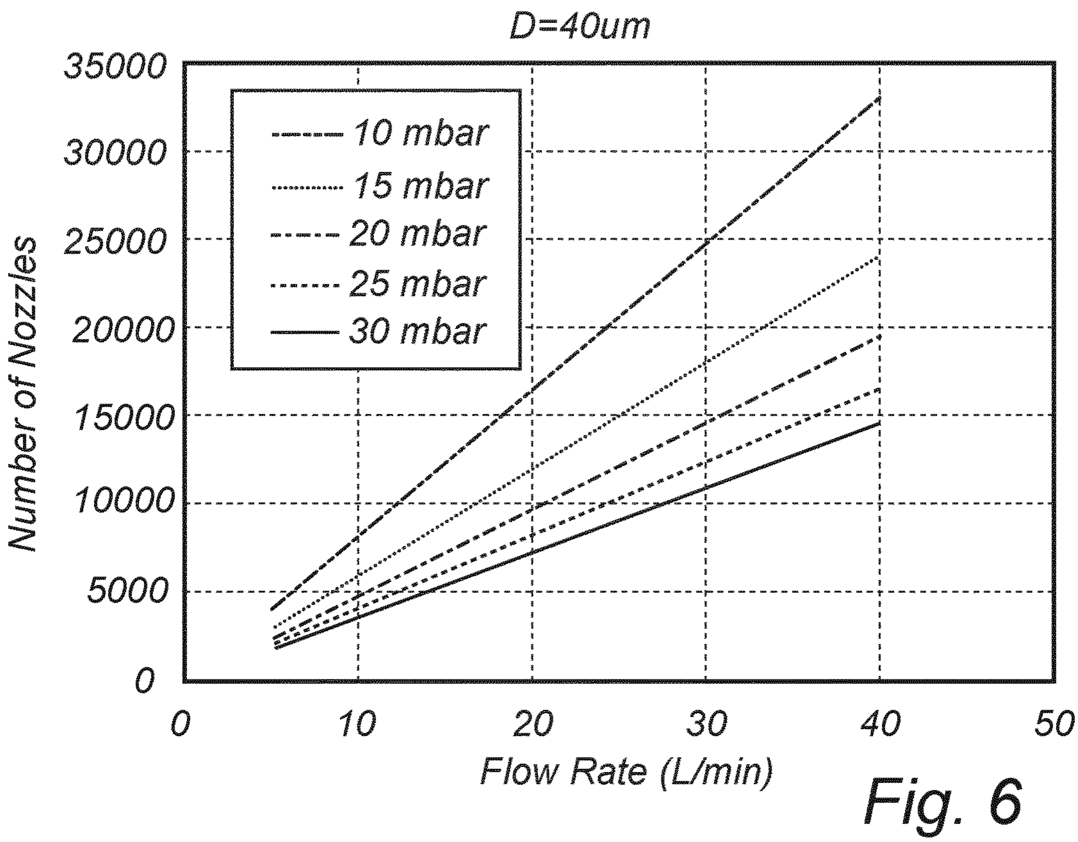
Figure 7:
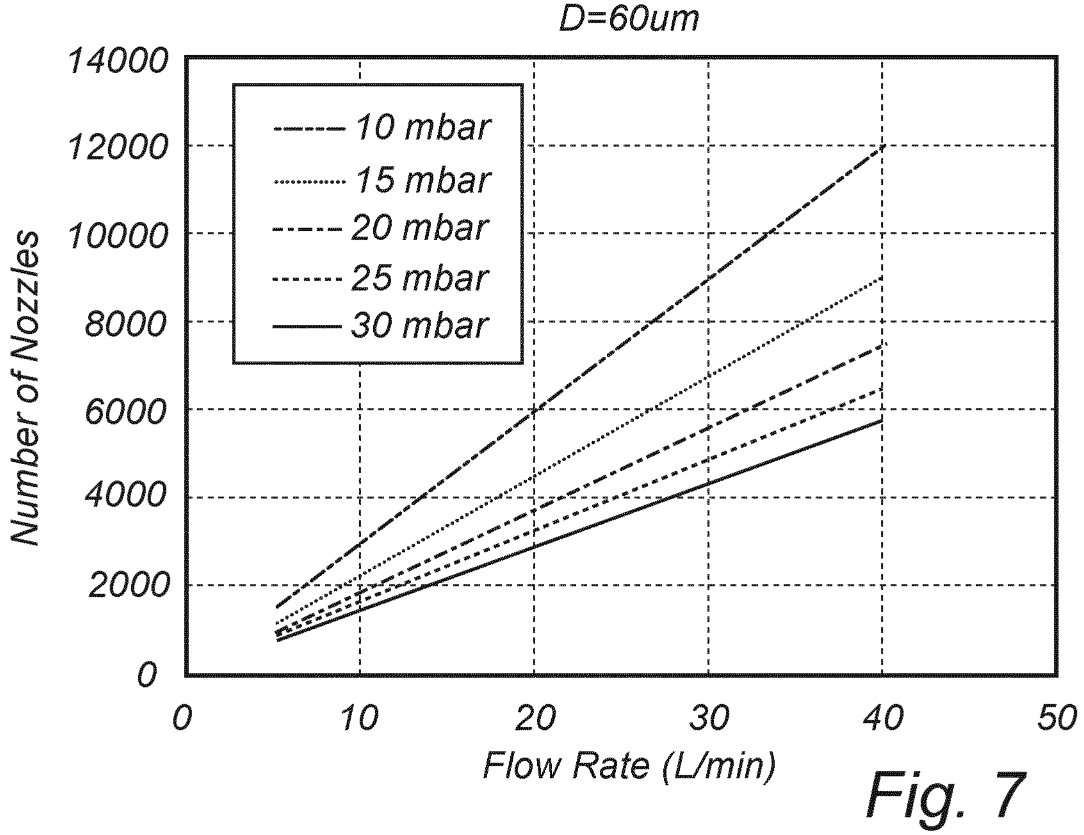

Referring now to FIG. 4, the calculated particle size that results in a collection efficiency of 50% (i.e., $\sqrt{Stk} \approx 0.48$) is plotted as a function of supply pressure. In general, smaller diameters result in better capture efficiency at a given supply pressure. However, at a supply pressure of 20 mbar and a nozzle diameter below approximately 20 μm, the Reynolds number drops below 10, which is in range that inertial impaction is not expected to be very effective. For nozzles above approximately 150 μm diameter, the collection efficiency at a 300 nm droplet size is not expected to be very high. Furthermore, larger diameters need higher supply pressures to reach the same collection efficiency.

If collection of small droplets, such as droplets down to a size of 300 nm is not important, a larger size of the nozzle diameter may be accepted. Also, the size of the nozzle diameter may be selected in relation to ease of manufacturing of the collecting device 200.

Figure 8:
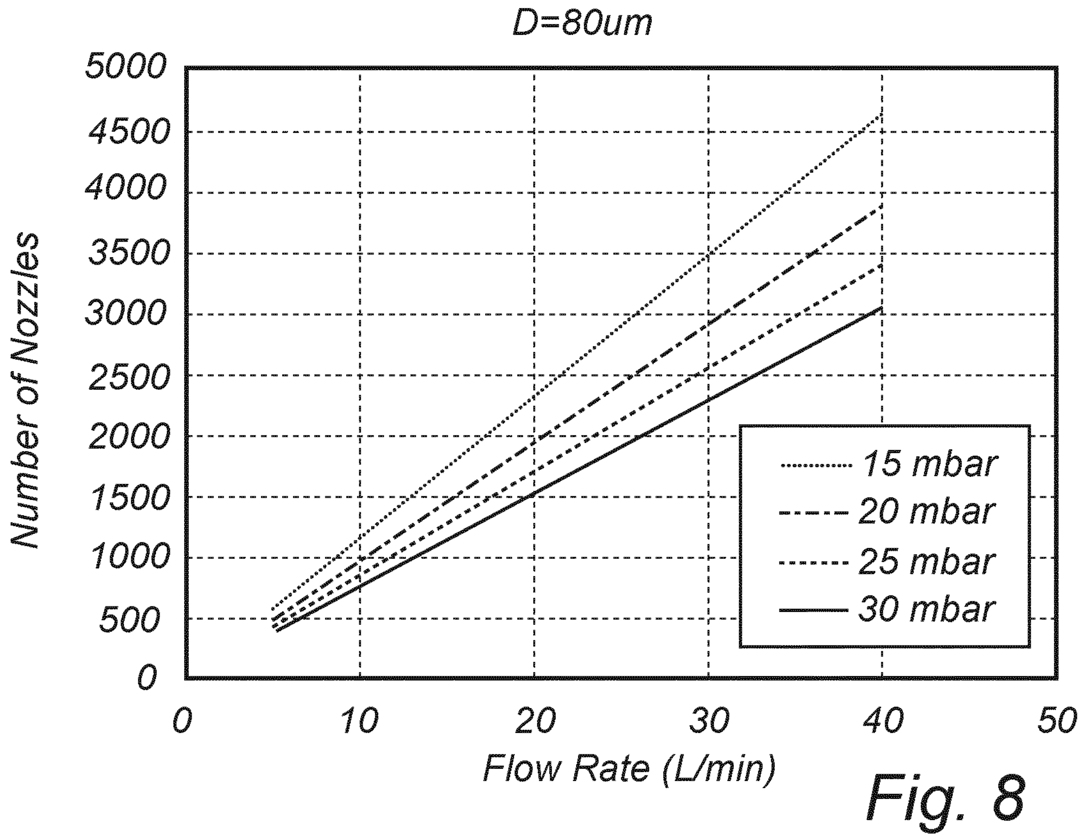
Figure 9:
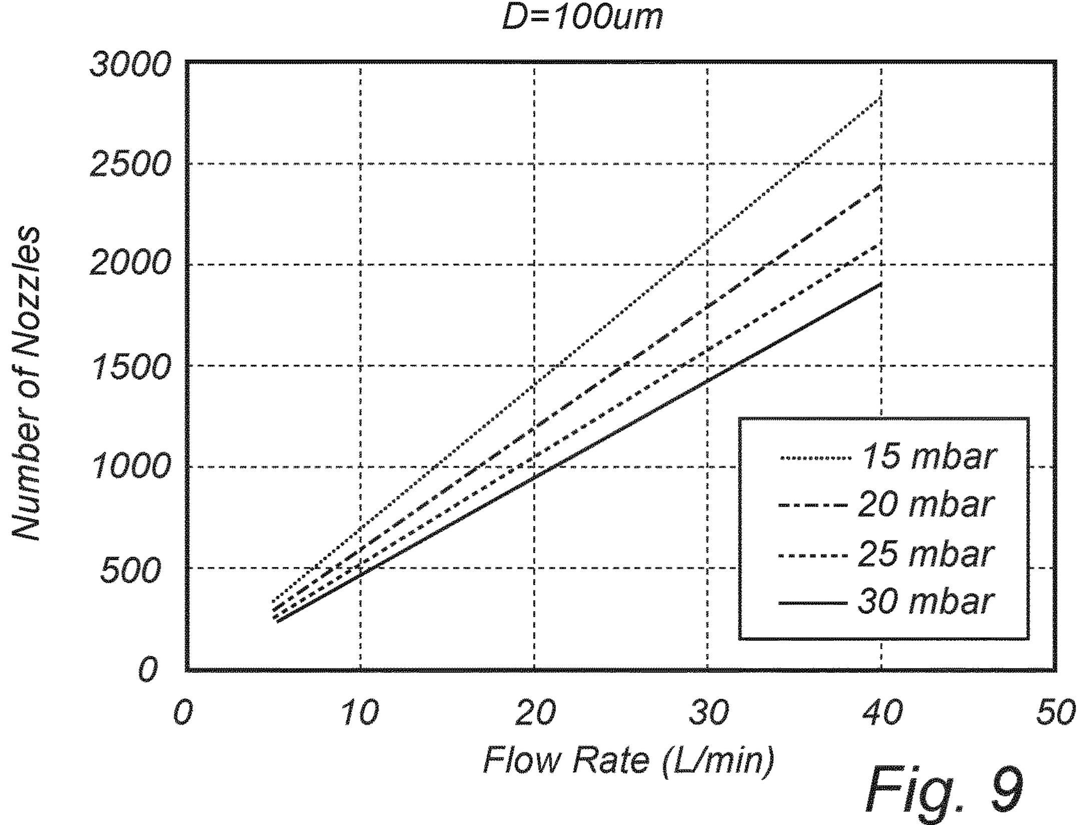
Figure 10:
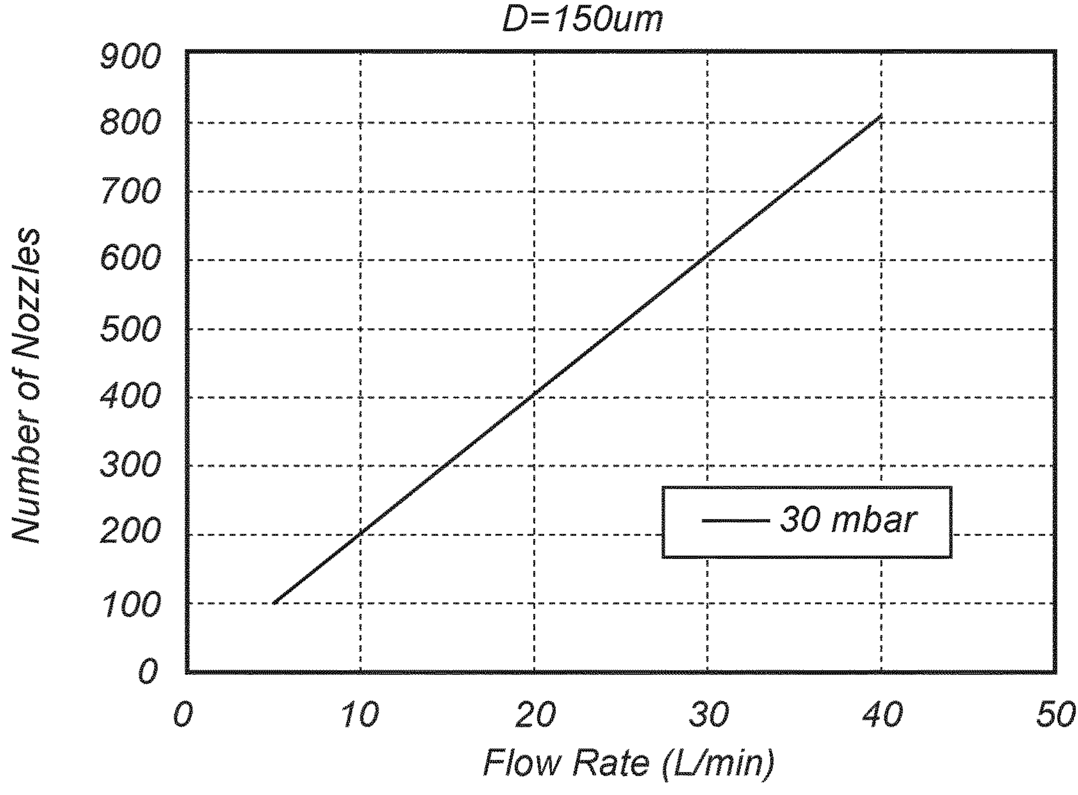

Referring now to FIGS. 5-10, the number of nozzles needed as a function of the target flow rate is indicated for different supply pressures and nozzle sizes. As can be seen in FIGS. 5-10, the number of nozzles needed is larger for smaller supply pressures being used. Also, the number of nozzles is larger if a larger flow rate is desired. Typically, an air flow rate of less than 40 liters/min may be desired so as to allow the person to provide the sample with relative ease. As seen in FIGS. 8-10, no indication is given for the smallest supply pressures. This is due to that, using nozzles with a diameter size of 80 μm or larger, a supply pressure of 10 mbar or even higher for larger diameter sizes will not be sufficient to capture particles as small as 300 nm with an efficiency of 50%.

Based on the information in FIGS. 5-10, the number of inlet nozzles 210 of interest is summarized in Table 1 below.

TABLE 1

| Nozzle Diameter (um) | Number of Nozzles |
|---|---|
| 20 | Between 6,900 and 280,000 |
| 40 | Between 1,300 and 33,000 |
| 60 | Between 530 and 12,000 |
| 80 | Between 280 and 5,000 |
| 100 | Between 170 and 2,800 |
| 150 | Between 100 and 810 |

Figure 11:
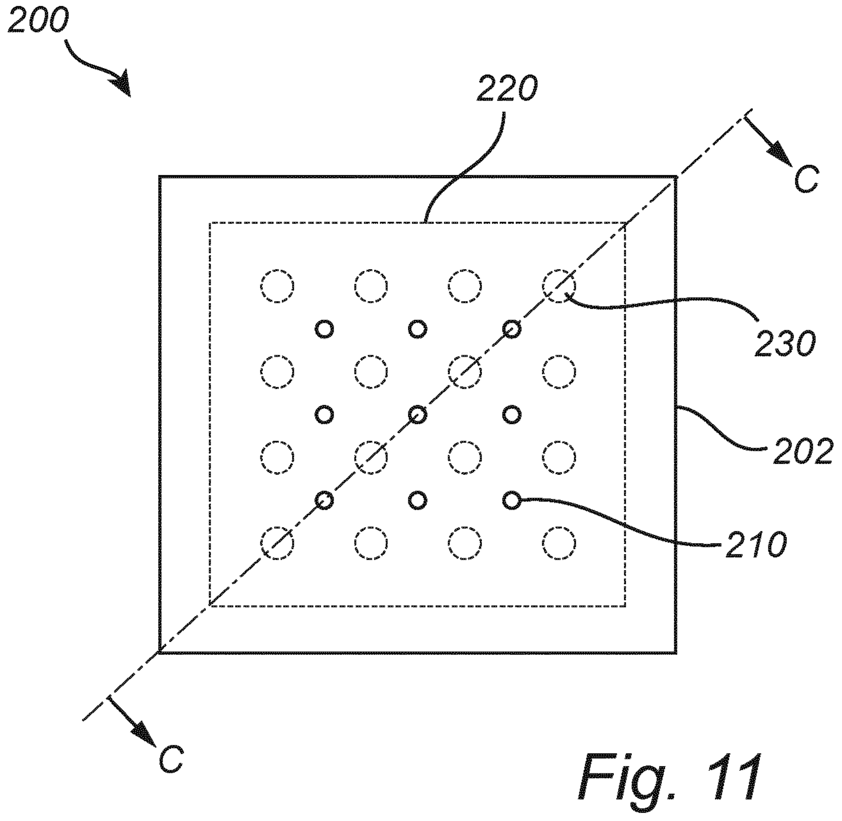
FIG. 11 is a schematic top view of a collecting device according to an embodiment.
Figure 12:
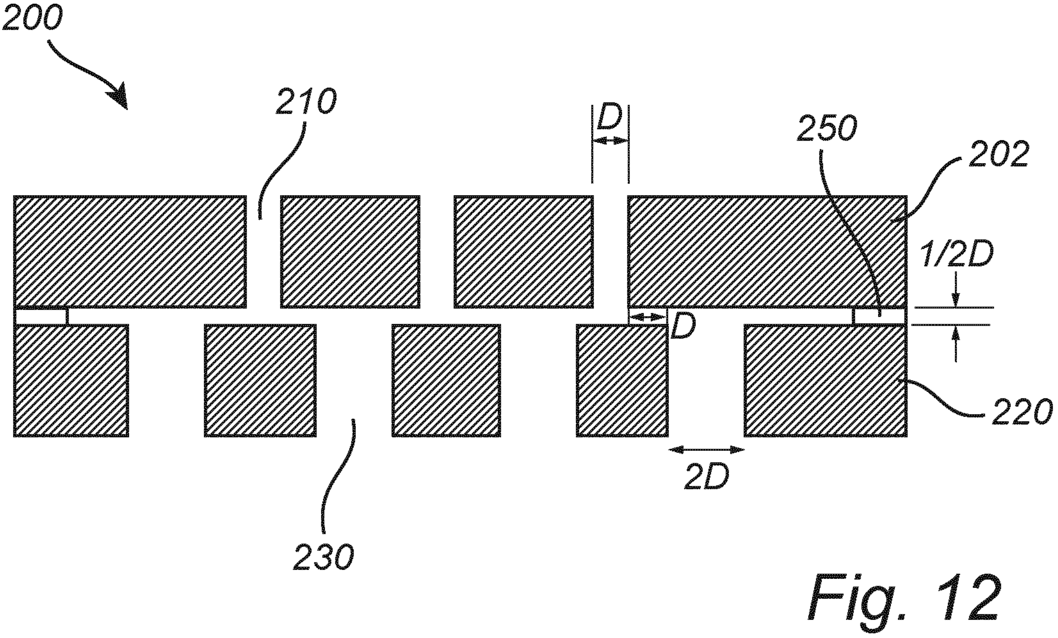
FIG. 12 is a schematic cross-sectional view of the collecting device, wherein the cross-section is taken along line C-C in FIG. 11.

Referring now to FIGS. 11-12, a schematic top view and cross-sectional view of an embodiment of the collecting device 200 for collecting particles are shown. FIG. 12 is a cross-section taken along line C-C in FIG. 11. The inlet nozzles 210 are located in the first layer 202. The incoming sample flow of air 104 comprising the exhaled aerosol and/or droplets flows through the inlet nozzles 210 and impinges on the second layer 220 (indicated by dashed lines in FIG. 11), where the airborne particles are captured. The first layer 202 and the second layer 220 are separated by a spacer 250. After the flow of air impinges on the second layer 220, the flow of air flows through outlet nozzles 230 in the second layer 220.

In FIG. 12, typical relations between sizes of features that may be suitable in the collecting device 200 are indicated. The spacer 250 may thus have a thickness approximately ½ D, wherein D is the diameter size of the inlet nozzle 210. The outlet nozzles 230 may typically be spaced a distance >D away from the inlet nozzles 210. Further, the outlet nozzles 230 may have a diameter that is twice the inlet nozzle diameter.

In other embodiments, the inlet nozzle 210 may have a diameter size of 100-200 μm, the spacer 250 may have a thickness of 20-100 μm, the outlet nozzles 230 may be spaced 20 μm away from the inlet nozzles 210 and the outlet nozzles may have a diameter size of 100-300 μm.

One of the two layers 202, 220 is preferably fabricated in silicon due to its thermal properties to enable rapid temperature cycling, which may be advantageous in providing reactions in the analysis chamber 240. For instance, temperature cycling may be needed in polymerase chain reaction (PCR), which may be useful in preparing a sample for testing for presence of SARS-CoV-2. Thanks to enabling rapid temperature cycling, ultrafast PCR may be provided.

Referring again to FIG. 2, a heater and temperature sensor or at least contacts for a heater 260 and a temperature sensor 262 can be fabricated onto one side of the silicon layer, here shown as second layer 220, for thermal control. The other substrate, here shown as first layer 202, may be fabricated in a transparent material, such as glass, poly(methyl methacrylate) (PMMA), or cyclo olefin polymer (COP) to enable optical readout. For instance, an optical measurement may detect fluorescently tagged DNA.

The spacer 250 can either be a glue, double sided-adhesive tape, or in case of silicon/glass layers 202, 220, the spacer 250 can be integrated into one of the layer materials to enable anodic, fusion, or laser bonding of the two layers 202, 220.

In addition to the inlet nozzles 210 and outlet nozzles 230, an additional reagent inlet may be provisioned in the design to enable filling of the analysis chamber 240 with a liquid reagent, such as a PCR reagent. It is envisioned that after a person exhales breath through the sample collector 100, the sample collector 100 is then placed inside an analysis instrument that performs an assay, e.g. a PCR assay. The analysis instrument may seal the inlet nozzles 210 and outlet nozzles 230 and may pump the reagents into the analysis chamber 240. An additional vent may need to be provisioned in the design to allow the air to escape the analysis chamber 240 during reagent filling.

Figure 13:
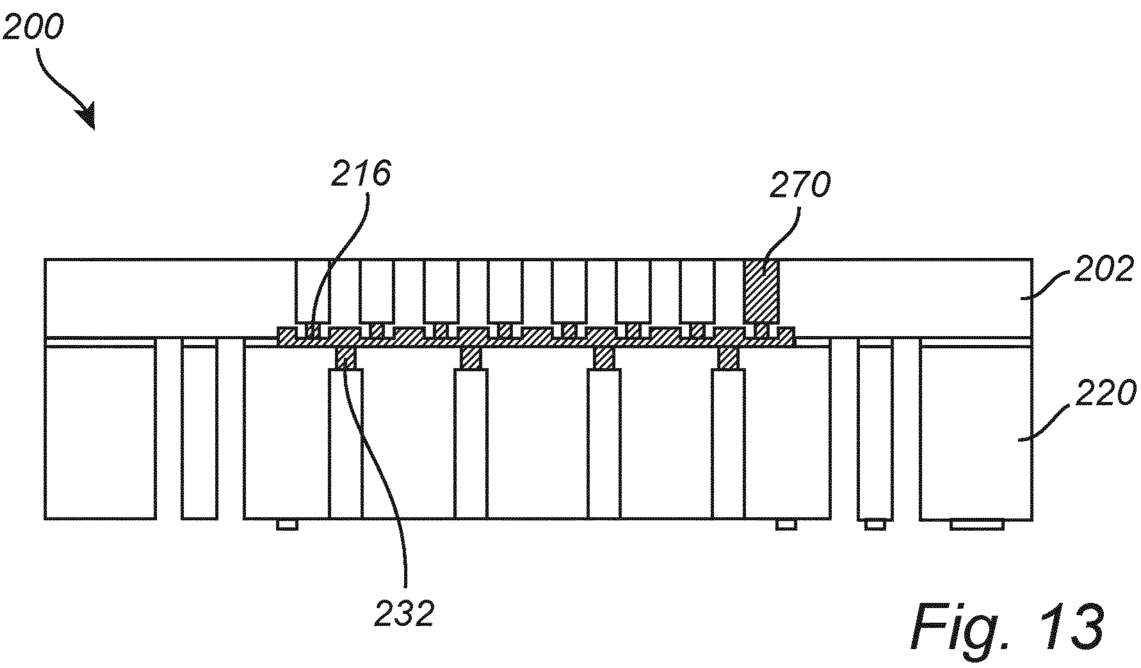
FIGS. 13 and 14 are schematic cross-sectional views of the collecting device illustrating the collecting device in different stages of analysis of a sample within an analysis chamber of the collecting device.
Figure 14:
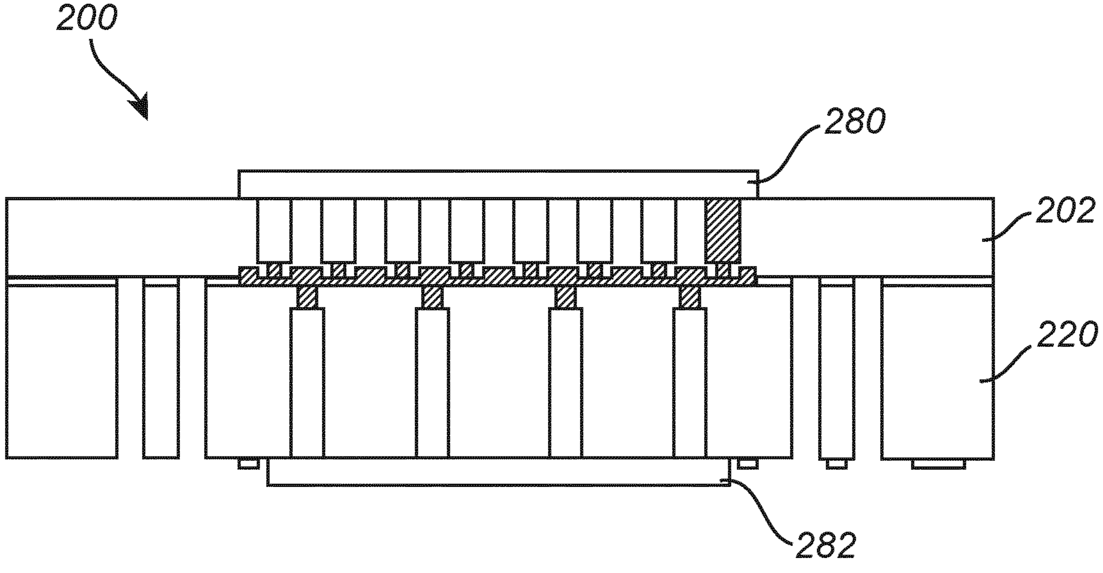

Referring now to FIGS. 13-14, the collecting device 200 is shown through different stages of analysis in the analysis chamber 240. The stages shown in FIGS. 13-14 may be performed while the sample collector 100 with the collecting device 200 is placed in an analysis instrument.

First, particles are collected in the particle collection chamber, which in this embodiment also forms the analysis chamber 240. As shown in FIG. 13, a liquid reagent is provided into the analysis chamber 240 through a reagent inlet 270.

The inlet nozzles 210 as well as the outlet nozzles 230 may have constrictions 216 and 232, wherein the constrictions 216, 232 have a smaller cross-sectional size than a remaining portion of the inlet nozzles 210 and outlet nozzles 230, respectively. The constrictions 216, 232 may function as capillary stops for sealing the analysis chamber 240 for preventing liquid reagent from escaping the analysis chamber 240.

As shown in FIG. 14, additional seals 280, 282 may be provided to seal the analysis chamber 240 and prevent evaporation from the analysis chamber 240 during thermal cycling. It should be realized that the additional seals 280, 282 may be pre-mounted on the collecting device 200 or in the sample collector 100 and may be arranged in a sealing position e.g. by a linear or rotational movement. Instead of arranging physical sealing layers, as indicated by seals 280, 282 on opposite sides of the collecting device 200, valves within the collecting device 200 may be activated for sealing the analysis chamber 240. Furthermore, if the inlet nozzles 210 and outlet nozzles 230 are sufficiently small, no additional sealing may be necessary.

The collected particles and the reagent in the analysis chamber 240 may then be subject to thermal cycling, which may for instance be advantageous in achieving ultrafast PCR.

The collecting device 200 may be configured to provide an analysis chamber 240 defining a small volume. Thus, since the analysis chamber 240 is small, the sample in the analysis chamber 240 has a small volume allowing rapid changes of temperature of the sample to allow rapid thermal cycling.

After reactions have been caused in the analysis chamber 240, a measurement based on light may be performed. The measurement may involve illuminating the analysis chamber 240 with a particular wavelength of light and detecting fluorescent light being emitted from the analysis chamber 240.

Figures 15A, 15B, 15C, 16:
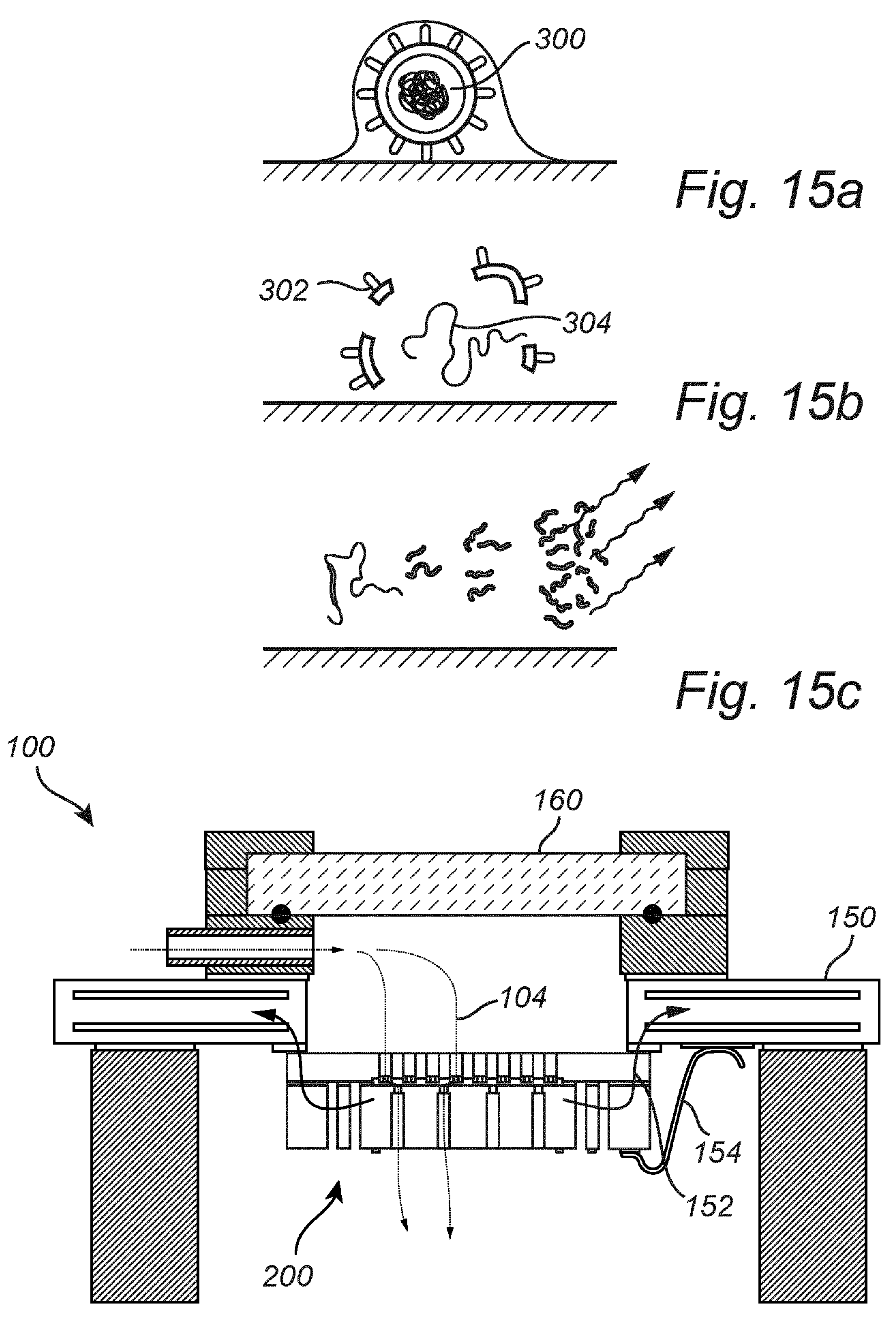
FIGS. 15*a*-*c* are schematic views illustrating a molecular assay to be performed in the analysis chamber.
FIG. 16 is a partial cross-section through a sample collector according to an embodiment.

Referring now to FIGS. 15*a*-*c*, an assay that may be performed in the analysis chamber 240 for detecting presence of SARS-CoV-2 in the exhaled breath of the person will be described.

As shown in FIG. 15*a*, aqueous particles, such as droplets, from breath are collected by impaction in the analysis chamber. The particles may include viral particles, such as SARS-CoV-2 viral particles 300.

As shown in FIG. 15*b*, a single reagent mix is added and a thermal lysis step is performed. This implies that a protein shell 302 is removed and viral RNA 304 is made available in the analysis chamber 240.

As shown in FIG. 15*c*, the viral RNA is converted to DNA by reverse transcriptase followed by amplification by quantitative PCR. Fast thermal cycling is provided in order to provide a fast PCR process.

Referring now to FIG. 16, a partial cross-section through the sample collector 100 is shown. As shown in FIG. 16, a flow of air 104 may be guided through the collecting device 200 for capturing particles in the analysis chamber 240.

Further, as shown in FIG. 16, the collecting device 200 may be configured to be connected to printed circuit board (s) on which the control unit 130 may be arranged. The connection of the collecting device 200 to the printed circuit boards 150 may allow heat to be extracted as indicated by arrow 152 from the collecting device 200 during thermal cycling in the analysis chamber 240.

The collecting device 200 may further be connected to the printed circuit board 150 (and the control unit 130) through a wire bond 154, which may allow control of a heater 260 on the collecting device 200 and may allow feedback by a temperature sensor 262 to the control unit 130.

As shown in FIG. 16, the sample collector 100 may comprise a transparent window 160 through a wall of the sample collector 100. This implies that a measurement based on light may be performed in the analysis instrument through the transparent window 160. As shown in FIG. 16, the collecting device 200 may further be mounted in the sample collector 160 in relation to the transparent window 160 so as to allow optical access to the collecting device 200 through the transparent window 160.

Figures 17, 18:
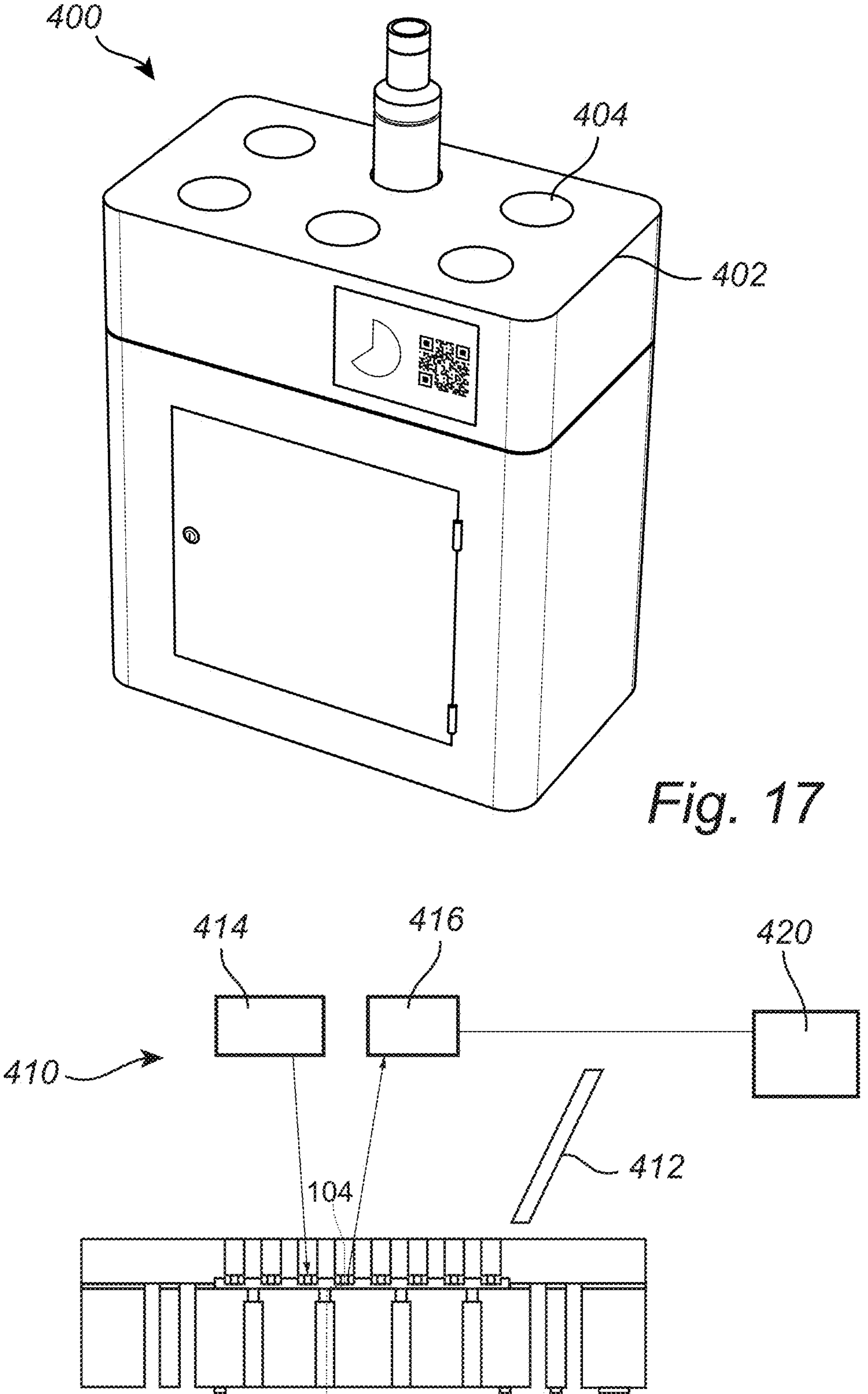
FIG. 17 is a schematic view of an analysis instrument according to an embodiment.
FIG. 18 is a schematic view of an analysis unit of the analysis instrument according to an embodiment.

Referring now to FIG. 17, an analysis instrument 400 will be described. The analysis instrument 400 comprises a holder 402 defining a plurality of receiving positions 404 for receiving sample collectors 100.

The analysis instrument 400 may be configured to simultaneously analyze samples in the sample collectors 100 in each receiving position 404. As further described in relation to FIG. 18, the analysis instrument 400 may comprise a plurality of analysis units 410, wherein each analysis unit 410 is associated with a receiving position.

In each analysis unit 410, there may be a reagent provider 412 for providing a liquid reagent to the collecting device 200 for ensuring that a liquid reagent is inserted into the analysis chamber 240. The reagent provider 412 may receive liquid reagent from a storage within the analysis instrument 400, wherein reagents for all analysis units 410 may be commonly stored.

Once a reagent has been provided into the analysis chamber 240, the sample may be subject to thermal cycling. Heating for the thermal cycling may be provided through a heater 260 on the collecting device 200 controlled by a control unit 130 in the sample collector 100. The control unit 130 may receive a control signal from the analysis unit 410 to trigger the thermal cycling.

The analysis unit 410 may further comprise a light source 414 for illuminating the sample in the analysis chamber 240. Further, the analysis unit 410 may comprise a light detector 416 for detecting light from the sample, e.g. for detecting fluorescent light emitted by the sample.

Measurement signals from the light detector 416 may be transmitted to a processing unit 420 which may be shared by the analysis units 410. The processing unit 420 may process the measurement signals in order to determine an analysis result, which may be used for determining whether the person is infected by a disease.

The processing unit 420 may be implemented as a general-purpose processing unit, such as a central processing unit (CPU), which may execute the instructions of one or more computer programs in order to implement the functionality of the processing unit 420. The processing unit 420 may alternatively be implemented as firmware arranged e.g. in an embedded system, or as a special-purpose circuitry for providing only specific logical operations. Thus, the processing unit 420 may be provided in the form of an ASIC or FPGA.

The processing unit 420 may further comprise a non-volatile memory. The memory may store application(s), which may be loaded into a working memory of the processing unit 420 for controlling the processing performed by the processing unit 420.

According to an embodiment, the analysis instrument 400 is configured to transport the sample collector to a waste bin after analysis of the sample.

Thus, the analysis instrument 400 may automatically remove sample collectors 100 after an analysis has been performed. This implies that no manual handling of sample collectors may be needed after the sample collector has been placed in the receiving position.

For instance, the receiving position 404 may be provided with a lid leading to a passageway from the receiving position 404 to the waste bin, such that the lid may be opened to transport the sample collector 100 away from the receiving position 404 when the analysis has been performed.

According to an embodiment, the analysis instrument 400 may further comprise a user interface for identification of a user, wherein the user interface is configured to allow for touch-less input by the user.

In order to avoid that a disease is spread by people being in contact with the analysis instrument 400, the analysis instrument 400 may be configured for touch-less input.

The user interface may for instance comprise a reader for reading a code, such that a user may by means of a smartphone or another device present a QR-code or another code to the reader.

The user interface may alternatively be a tag reader, which may be configured to read an individual tag, which may identify a user. For instance, at a company facility, employees may anyway wear an individual tag based e.g. on radio-frequency identification (RFID) technology, and such tags may be used for identifying a user through the touch-less input to the analysis instrument.

According to an embodiment, the analysis instrument 400 further comprises a communication unit for communicating a result of analysis of the sample to a remote unit specified by a user.

Thus, the user may receive the analysis result directly to a specified remote unit. This may enable analysis results to be provided directly to a phone of the user, such that the user may have immediate access to the analysis result. For instance, a user may not be admitted through an entrance before the user may show a negative analysis result, i.e. that the user is not infected.

Figure 19:
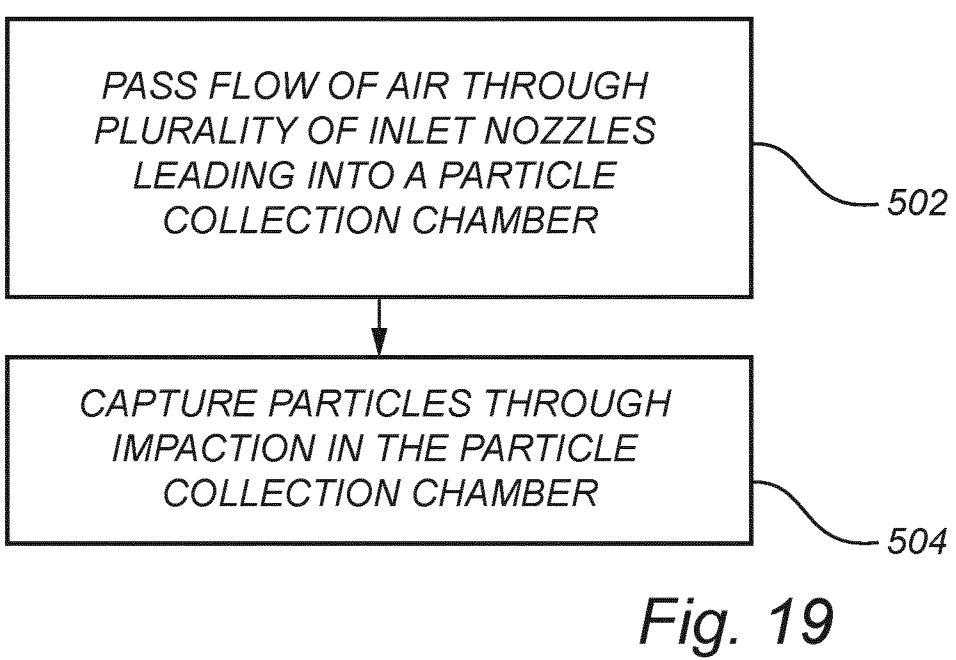
FIG. 19 is a flow chart of a method for collection of particles for analysis according to an embodiment.

Referring now to FIG. 19, a method for collection of particles for analysis will be described.

The method comprises passing 502 a flow of air 104 carrying airborne particles through a plurality of inlet nozzles 210 through a first layer 202 of a collecting device 200 for passing the flow of air 104 from the inlet nozzles 210 into a particle collection chamber 240.

The method further comprises capturing 504 airborne particles through impaction in the particle collection chamber 240 by the flow of air 104 being passed into the particle collection chamber 240 impinging on a first surface 222 of the second layer 220 facing the first layer 202 in the particle collection chamber 240. The airborne particles are captured in a particle collection chamber 240 which provides optical access for performing a measurement, based on light, of airborne particles collected in the particle collection chamber 240 at a first measurement position arranged such that the second layer 202 is between the second side of the particle collection chamber 240 and the first measurement position or at a second measurement position, which is arranged at an opposite side to the first measurement position in relation to the second side of the particle collection chamber 240.

According to the method airborne particles are captured in a particle collection chamber, which allows measurements based on light to be performed on the surface on which airborne particles are captured. This implies that efficient capture of particles may be performed and that measurements for analysis of the captured particles may be performed without a need of removing the captured particles from the surface on which they are captured.

Figure 20:
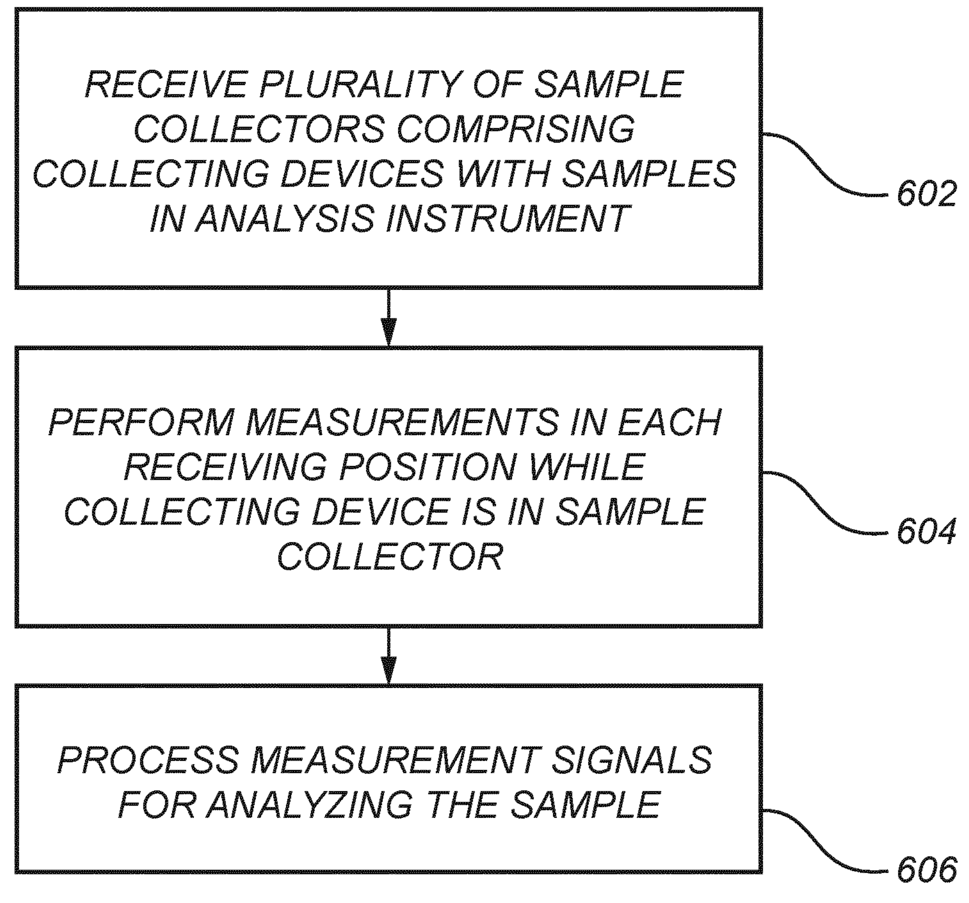
FIG. 20 is a flow chart of a method for analysis of samples of particles according to an embodiment.

Referring now to FIG. 20, a method for analysis of samples of particles in human breath will be described.

The method comprises receiving 602 a plurality of sample collectors 100 in a plurality of receiving positions 404 of an analysis instrument 400, wherein each sample collector 100 comprises a collecting device 200 carrying a sample of airborne particles being captured in an analysis chamber 240 in the collecting device 200 by impaction.

The method further comprises performing 604 measurements based on light in each of the receiving positions 404, wherein a light detector 416 detects light from the sample in the analysis chamber 240 while the collecting device 200 is arranged in the sample collector 100.

The method further comprises processing 606 a signal from the light detector 416 for analyzing the sample.

Thanks to the method, a sample collected in a sample collector 100 may be analyzed without a need of removing a collecting device 200 from the sample collector 100. This ensures that undesired handling of a sample collector 100 which may be contaminated by infectious particles may be avoided.

As described above, the processing of the signal may be performed in many different manners for analyzing the sample, such as detecting an amount of received fluorescent light to determine a quantity of a particle or substance of interest within the sample. Alternatively, the light signal from the light detector 416 may be an image of the sample and the processing may include image processing for analyzing the sample.

The sample may be subject to preparatory treatment before measurements are performed. All steps for preparatory treatment may be performed while the collecting device 200 is arranged in the sample collector 100.

The method may comprise introducing a liquid reagent into the analysis chamber 240.

The method may comprise providing thermal energy to the analysis chamber 240, which may control a reaction in the analysis chamber 240.

The method may comprise providing thermal energy for thermal lysis to expose RNA of SARS-CoV-2 in the captured particles, converting the RNA to DNA using reverse transcriptase based on the reagent and providing thermal cycling for amplification of the DNA using quantitative PCR.

In the above the inventive concept has mainly been described with reference to a limited number of examples. However, as is readily appreciated by a person skilled in the art, other examples than the ones disclosed above are equally possible within the scope of the inventive concept, as defined by the appended claims.

Although analysis for determining presence of SARS-CoV-2 is mainly described, it should be realized that the collecting device 200, sample collector 100, analysis instrument 400 and methods may alternatively be used for determining presence of another particle, such as determining presence of influenza particles, or for a completely different type of analysis of captured particles.

The invention claimed is:

1. A collecting device for collection of particles and presentation of collected particles for analysis, said collecting device comprising:

a first layer and a second layer, wherein the first layer and the second layer are arranged to be spaced apart for defining a particle collection chamber between the first and the second layer, wherein the particle collection chamber has a first and a second side defined by the first layer and the second layer, respectively;

wherein the first layer comprises a first surface configured to receive a flow of air carrying airborne particles and a second surface facing the second layer, wherein the first layer comprises a plurality of inlet nozzles having a first end at the first surface of the first layer and a second end at the second surface of the first layer, wherein the inlet nozzles are configured to extend through the first layer for transporting the flow of air therethrough from the first end to the second end;

wherein the second ends of the inlet nozzles are configured to face a first surface of the second layer for capturing airborne particles in the flow of air entering the particle collection chamber through the second ends of the inlet nozzles by impaction of airborne particles on the first surface of the second layer;

wherein the second layer comprises a plurality of outlet nozzles, wherein the outlet nozzles have a first end at the first surface of the second layer and a second end at a second surface of the second layer and the outlet nozzles are configured to extend through the second layer for transporting the flow of air therethrough from the first end to the second end, wherein a position of the first ends of the outlet nozzles is shifted with respect to a position of the second ends of the inlet nozzles such that the outlet nozzles are not collinear with the inlet nozzles;

wherein the collecting device is configured to provide optical access for performing a measurement, based on light, of airborne particles collected in the particle collection chamber at a first measurement position arranged such that the second layer is between the second side of the particle collection chamber and the first measurement position or at a second measurement position, which is arranged at an opposite side to the first measurement position in relation to the second side of the particle collection chamber.

2. The collecting device according to claim 1, further comprising a reagent inlet for providing a liquid reagent into the particle collection chamber.

3. The collecting device according to claim 2, wherein the collecting device is configured to seal the particle collection chamber for trapping a liquid sample in the particle collection chamber.

4. The collecting device according to claim 3, wherein the inlet nozzles comprise a first portion extending from the first end to a constriction arranged at the second end of the inlet nozzles, wherein the inlet nozzles has a smaller cross-sectional size in the constriction than in the first portion for forming a capillary force to maintain the liquid sample in the particle collection chamber.

5. The collecting device according to claim 3, wherein the collecting device comprises valves for sealing the particle collection chamber.

6. The collecting device according to claim 1, wherein the inlet nozzles are configured at the second end to have a diameter in a range of 20-300 μm.

7. The collecting device according to claim 1, wherein a number of inlet nozzles is larger than 100.

8. The collecting device according to claim 1, wherein the collecting device is configured to provide a collection efficiency of at least 50% for particles having a diameter larger than 300 nm when the collecting device receives a flow of air having a pressure in a range of 10-30 mbar.

9. The collecting device according to claim 1, further comprising at least one contact arranged on the first or the second layer for receiving energy to provide heating to a liquid sample in a particle collection chamber.

10. The collecting device according to claim 1, wherein the collecting device comprising a heat source is configured for receiving a liquid reagent to be mixed with the collected particles in the particle collection chamber, receiving heat from the heat source for thermal lysis to expose RNA of severe acute respiratory syndrome coronavirus 2, SARS-COV-2, in the collected particles, converting the RNA to DNA using reverse transcriptase based on the liquid reagent in the particle collection chamber and providing thermal cycling from the heat source for amplification of the DNA using a quantitative polymerase chain reaction.

11. A sample collector comprising:

the collecting device according to claim 1;

a mouthpiece for receiving a flow of air from exhalation by a human being;

wherein the collecting device is arranged in the sample collector to receive the flow of air from the mouthpiece.

12. The sample collector according to claim 11, further comprising a flow meter for providing a measure of a volume of air being provided through the mouthpiece.

13. The sample collector according to claim 11, wherein at least a portion of a wall of the sample collector is transparent for enabling analysis of airborne particles in the particle collection chamber of the collecting device by a measurement based on light through the transparent portion of the wall of the sample collector.

14. An analysis instrument for analysis of particles in a human breath, said analysis instrument comprising:

a holder defining a plurality of receiving positions for receiving a plurality of sample collectors according to claim 11;

a plurality of analysis units, wherein one analysis unit is associated with each receiving position, wherein each analysis unit comprises a light source configured to illuminate a sample in the particle collection chamber of the collecting device of the sample collector, a light detector for detecting light produced from the illuminated sample; and circuitry configured to produce a signal from the light detector, and a processor configured to process the signal from the light detector for analyzing the sample.

15. A method for analysis of samples of particles in human breath; said method comprising:

receiving a plurality of sample collectors in a plurality of receiving positions of an analysis instrument, wherein each sample collector comprises a collecting device carrying a sample of airborne particles being captured in a particle collection chamber in the collecting device according to claim 1 by impaction therein;

performing measurements based on light in each of the receiving positions, wherein a light detector detects light from the sample in the particle collection chamber while the collecting device is arranged in the sample collector; and processing a signal from the light detector for analyzing the sample.

16. The method according to claim 15, further comprising, before performing measurements, introducing a liquid reagent in the particle collection chamber, while the collecting device is arranged in the sample collector.

17. The method according to claim 16, further comprising, before performing measurements and after introducing a liquid reagent, providing thermal energy to the particle collection chamber from a heat source, while the collecting device is arranged in the sample collector, for controlling a reaction in the particle collection chamber.

18. The method according to claim 17, wherein the thermal energy is provided from the heat source for thermal lysis to expose RNA of severe acute respiratory syndrome coronavirus 2, SARS-COV-2, in the captured particles, converting the RNA to DNA using reverse transcriptase based on the reagent in the particle collection chamber and providing thermal cycling from the heat source for amplification of the DNA using quantitative polymerase chain reaction.

19. A method for collection of particles for analysis, said method comprising:

passing a flow of air carrying airborne particles through a plurality of inlet nozzles through a first layer of a collecting device for passing the flow of air from the inlet nozzles into a particle collection chamber, wherein the particle collection chamber has a first and a second side defined by the first layer and a second layer, respectively; and capturing airborne particles through impaction in the particle collection chamber by the flow of air being passed into the particle collection chamber impinging on a first surface of the second layer facing the first layer in the particle collection chamber;

wherein the second layer comprises a plurality of outlet nozzles, wherein the outlet nozzles have a first end at the first surface of the second layer and a second end at a second surface of the second layer and the outlet nozzles are configured to extend through the second layer for transporting the flow of air therethrough from the first end to the second end, wherein a position of the first ends of the outlet nozzles is shifted with respect to a position of the second ends of the inlet nozzles such that the outlet nozzles are not collinear with the inlet nozzles;

wherein the particle collection chamber provides optical access for performing a measurement, based on light, of airborne particles collected in the particle collection chamber at a first measurement position arranged such that the second layer is between the second side of the particle collection chamber and the first measurement position or at a second measurement position, which is arranged at an opposite side to the first measurement position in relation to the second side of the particle collection chamber.

* * * * *